(12) United States Patent
Hosoya et al.

(10) Patent No.: US 9,157,069 B2
(45) Date of Patent: Oct. 13, 2015

(54) METHOD OF PRODUCING PANCREATIC HORMONE-PRODUCING CELLS

(75) Inventors: Masaki Hosoya, Fujisawa (JP); Masanobu Shoji, Fujisawa (JP)

(73) Assignee: Takeda Pharmaceutical Company Limited, Osaka-Shi (JP)

( * ) Notice: Subject to any disclaimer, the term of this patent is extended or adjusted under 35 U.S.C. 154(b) by 71 days.

(21) Appl. No.: 13/814,878

(22) PCT Filed: Aug. 8, 2011

(86) PCT No.: PCT/JP2011/068487
§ 371 (c)(1),
(2), (4) Date: Feb. 7, 2013

(87) PCT Pub. No.: WO2012/020845
PCT Pub. Date: Feb. 16, 2012

(65) Prior Publication Data
US 2013/0210060 A1    Aug. 15, 2013

(30) Foreign Application Priority Data
Aug. 9, 2010   (JP) .................................. 2010-178523

(51) Int. Cl.
C12N 5/071         (2010.01)
G01N 33/50         (2006.01)
A61K 35/39         (2015.01)

(52) U.S. Cl.
CPC .............. *C12N 5/0676* (2013.01); *A61K 35/39* (2013.01); *G01N 33/507* (2013.01); *C12N 2501/115* (2013.01); *C12N 2501/16* (2013.01); *C12N 2501/385* (2013.01); *C12N 2501/727* (2013.01); *C12N 2506/02* (2013.01); *C12N 2506/45* (2013.01); *C12N 2513/00* (2013.01)

(58) Field of Classification Search
CPC .............. C12N 5/0676; C12N 2506/45; C12N 2501/727; C12N 2501/385; C12N 2501/115; C12N 2501/16; C12N 2506/02; C12N 2513/00; G01N 33/507; A61K 35/39
See application file for complete search history.

(56) References Cited

U.S. PATENT DOCUMENTS

| | | |
|---|---|---|
| 7,033,831 B2 | 4/2006 | Fisk et al. |
| 7,326,572 B2 | 2/2008 | Fisk et al. |
| 7,534,608 B2 | 5/2009 | Martinson et al. |
| 9,085,756 B2 | 7/2015 | Fisk et al. |
| 2003/0138948 A1 | 7/2003 | Fisk et al. |
| 2006/0040387 A1 | 2/2006 | Fisk et al. |
| 2008/0066197 A1 | 3/2008 | Ying et al. |
| 2008/0145889 A1 | 6/2008 | Fisk et al. |
| 2008/0171385 A1 | 7/2008 | Bergendahl et al. |
| 2009/0093055 A1 | 4/2009 | Fisk et al. |
| 2009/0130759 A1 | 5/2009 | Smith et al. |
| 2009/0170198 A1 | 7/2009 | Rezania |
| 2009/0325180 A1 | 12/2009 | Fisk et al. |
| 2010/0009442 A1 | 1/2010 | Sasai et al. |
| 2010/0015100 A1 | 1/2010 | Xu |
| 2010/0093760 A1 | 4/2010 | Yu et al. |
| 2010/0196916 A1 | 8/2010 | Fisk et al. |
| 2010/0255580 A1 | 10/2010 | Rezania |
| 2011/0065118 A1 | 3/2011 | Fisk et al. |
| 2011/0091869 A1 | 4/2011 | Sasai et al. |
| 2014/0342452 A1 | 11/2014 | Fisk et al. |

FOREIGN PATENT DOCUMENTS

| | | |
|---|---|---|
| CN | 103237886 A | 8/2013 |
| JP | 2006-500003 A | 1/2006 |
| JP | 2006-075022 A | 3/2006 |
| JP | 2008-099662 A | 5/2008 |
| JP | 2008-533984 A | 8/2008 |
| JP | 2009-225661 A | 10/2009 |
| JP | 2009-545302 A | 12/2009 |
| JP | 2010-516255 A | 5/2010 |
| WO | WO-2006/100490 A1 | 9/2006 |
| WO | WO-2008/015418 A2 | 2/2008 |
| WO | WO-2008/033408 A2 | 3/2008 |
| WO | WO-2008/035110 A1 | 3/2008 |

(Continued)

OTHER PUBLICATIONS

Sato et al. (2004) Nat. Med. 10:55-63.*

(Continued)

*Primary Examiner* — Thaian N Ton
(74) *Attorney, Agent, or Firm* — Mintz Levin Cohn Ferris Glovsky and Popeo, P.C.; David G. Conlin, Esq.

(57) ABSTRACT

Disclosed is a production method of pancreatic hormone-producing cells in a form that mimicks the pancreatogenesis, the method comprising subjecting stem cells to the following steps:

(1) cultivating stem cells in a medium containing a Rho kinase inhibitor, (2) cultivating the cells obtained in (1) in a medium containing a GSK3 inhibitor, (3) cultivating the cells obtained in (2) in a medium containing GSK3 inhibitor and an activator of activin receptor-like kinase-4,7, (4) forming a cell mass from the cells obtained in (3), and cultivating the cell mass in a suspension state in a medium, (5) cultivating the cells obtained in (4) in a medium containing a retinoic acid receptor agonist, an inhibitor of AMP-activated protein kinase and/or activin receptor-like kinase-2,3,6, an inhibitor of activin receptor-like kinase-4,5,7 and a cell growth factor, and (6) cultivating the cells obtained in (5).

4 Claims, 6 Drawing Sheets
(2 of 6 Drawing Sheet(s) Filed in Color)

(56) References Cited

FOREIGN PATENT DOCUMENTS

| WO | WO-2008/066199 A1 | 6/2008 |
| WO | WO-2008/089351 A1 | 7/2008 |
| WO | WO-2009/012428 A2 | 1/2009 |
| WO | WO-2009/018453 A1 | 2/2009 |
| WO | WO-2009/070592 A2 | 6/2009 |
| WO | WO-2009/148170 A1 | 12/2009 |
| WO | 2010/057039 A2 | 5/2010 |
| WO | WO-2011/081222 A1 | 7/2011 |
| WO | WO-2012027474 A1 | 3/2012 |

OTHER PUBLICATIONS

Humphrey et al. (2004) Stem Cells 22: 522-530.*
Li et al., Blood, 98: 335-342, 2001.*
Shiraki et al, Genes to Cells, 13:731-746, 2008.*
Wobus et al. (1997) J Mol Cell Cardiology 29:1525.*
Doetschman et al. (1985) J. Embryol. Exp. Morphology 87:27.*
Xu et al. (2002) Circulation Research 91:50t.*
Wobus et al. (1988) Biomed. Biochim Acta 12:965.*
Schuldiner (2000) PNAS 97:11307.*
Kramer et al. (2000) Mech. of Dev. 92:193.*
Johansson et al. (1995) Mol and Cell Biol. 15:141.*
Zhang et al., J. of Cell Science, 125: 5609-5620, 2012.*
Li and Ding, Trends in Pharmacological Sciences, 31(1): 36-45, 2009.*
Naujok et al., BMC Research Notes, 7: 1-8, 2014.*
European Search Report dated Feb. 19, 2014 in corresponding European Patent Application No. 11816507.5.
M. Hosoya et al., "Preparation of pancreatic β-cells from human iPS cells with small molecules", ISLETS, 4(3), pp. 249-252 (2012).
F.J. Najm et al., "Rapid and robust generation of functional oligodendrocyte progenitor cells from epiblast stem cells", Nature Methods, 8(11), pp. 957-962 (2011).
International Search Report (PCT/ISA/210) of PCT/JP2011/068487, issued Dec. 6, 2011.
English Translation of International Preliminary Report on Patentability Chapter I (PCT/IB/373), issued Mar. 12, 2013.
Takehara et al., Regenerative Medicine, 2009, vol. 8, p. 203.
Fukunaga et al., Dai 81 Kai Annual Meeting of the Japanese Biochemical Society, Dai 31 Kai, The Molecular Biology Society of Japan Nenkai Godo Taikai Program, Koen Yoshishu, 2008, p. 1P-1082.
A. Honda, et al. "Basic FGF and Activin/Nodal but not LIF signaling sustain undifferentiated status of rabbit embryonic stem cells", Exp. Cell Res., 2009, vol. 315, No. 12, p. 2033-2042.
K. Wrighton, et al. "Transforming Growth Factor β can stimulate Smad1 phosphorylation Independently of Bone Morphogenic Protein receptors", J. Biol. Chem., 2009, vol. 284, No. 15, p. 9755-9763.
P. Yu, et al. "Dorsomorphin inhibits BMP signals required for embryogenesis and iron metabolism", Nat. Chem. Biol., 2008, vol. 4, No. 1, pp. 33-41.
E. Kroon et al. "Pancreatic endoderm derived from human embryonic stem cells generates glucose-responsive insulin-secreting cells in vivo", Nature Biotechnology, 2008, vol. 26, non. 4, pp. 443-452.
K. D'Amour et al. "Production of pancreatic hormone-expressing endocrine cells from human embryonic stem cells", Nature Biotechnology, 2006, vol. 24, No. 11, p. 1392-1401.
W. Jiang, et al. "In Vitro derivation of functional insulin-producing cells from human embryonic stem cells", Cell Research, 2007, vol. 17, p. 333-344.
R. Maehr, et al. "Generation of pluripotent stem cells from patients with type 1 diabetes", PNAS 2009, vol. 106,No. 37, p. 15768-15773.
J. Shim et al., "Directed differentiation of human embryonic stem cells towards a pancreatic cell fate", Diabetologia, 2007, vol. 50, p. 1228-1238.
M. Nostro, et al. "Stage-specific signaling through TGfβ family members and WNT regulates patterning and pancreatic specification of human pluripotent stem cells", Development, 2011, vol. 138, p. 861-871.
A. Rezania et al., "Production of Functional Glucagon-Secreting α-Cells from Human Embryonic Stem Cells", Diabetes, 2011, vol. 60, pp. 239-247.
T. Thatava et al. "Indolactam V/GLP-1-mediated differentiation of human iPS cells into glucose-responsive insulin-secreting progeny", Gene Therapy, 2011, vol. 18, p. 283-293.
Yeung et al., "Improvement in Pancreatic Islet Function After co-Culture with Adult Human Pancreatic Mesenchymal Stem Cells is Cell Contact Dependent", International Society for Stem Cell Research (ISSCR), 2011, 9th Annual Meeting, Poster Board No. 1006.
Z. Alipio, et al. "Reversal of hyperglycemia in diabetic mouse models using induced-pluripotent stem (iPS)-derived pancreatic β-like cells", PNAS, 2010, vol. 107, No. 30, p. 13426-13431.
S. Chen et al., "A small molecule that directs differentiation of human ESCs into the pancreatic lineage", Nat. Chem. Biol. 2009, vol. 5, No. 4, p. 258-265.
C. Mayhew, et al. "Converting Human Pluripotent stem cells into Beta Cells: Recent advances and future challenges", Cur Opin Organ Transplant, 2010, vo. 15, No. 1, p. 54-60.
M. Johannesson, et al. "FGF4 and retonic acid direction differentiation of hESCs into PDX1-Expressing foregut Endoderm in a Time- and Concentration-Dependent Manner", PLOS ONE, 2009, 4 (3), e4794, pp. 1-13.
E. Zhu, et al. "Generation of pancreatic insulin-producing cells from rhesus monkey induced pluripotent stemc cells", Diabetologia, 2011, vol. 54, p. 2325-2336.
K. Tateishi, et al. "Generation of Insulin-secreting Islet-like clusters from Human skin fibroblasts", Journal of Biological Chemistry, 2008, vol. 283, No. 46, p. 31601-31607.
Force, Thomas et al., "Unique and Overlapping Functions of GSK-3 Isoforms in Cell Differentiation and Proliferation and Cardiovascular Development," The Journal of Biological Chemistry, vol. 284(15):9643-9647 (2009).
Laketa, Vibor et al., "High-Content Microscopy Identifies New Neurite Outgrowth Regulators," Molecular Biology of the Cell, vol. 18:242-252 (2007).
Lock, Lye T. et al., "Expansion and Differentiation of Human Embryonic Stem Cells to Endoderm Progeny in the Microcarrier Stirred-Suspension Culture," Tissue Engineering:Part A, vol. 15(8):2051-2063 (2009).
Osakada, Fumitaka et al., "In vitro differentiation of retinal cells from human pluripotent stem cells by small-molecule induction," Journal of Cell Science, vol. 122:3169-3179 (2009).
Pacary, Emilie et al., "Synergistic effects of CoCl2 adn ROCK inhibition on mesenchymal stem cell differentiation into neuron-like cells," Journal of Cell Science, vol. 119:2667-2678 (2006).

* cited by examiner

METHOD OF PRODUCING PANCREATIC HORMONE-PRODUCING CELLS

CROSS-REFERENCE TO RELATED APPLICATIONS

This application is the national phase application pursuant to 35 U.S.C. §371 of International Application No. PCT/JP2011/068487, filed Aug. 8, 2011, which claims the benefit of priority of Japanese Patent Application No. 178523/2010, filed Aug. 9, 2010. These applications are hereby incorporated herein by reference in their entireties.

TECHNICAL FIELD

The present invention relates to a production method of pancreatic hormone-producing cells and a medicament comprising the pancreatic hormone-producing cells obtained by the production method and the like.

BACKGROUND OF THE INVENTION

Pancreas has endocrine glands (endocrine cells) and exocrine glands (exocrine cells), and is an organ playing an important role by the both cells. Exocrine cells mainly play a role of secreting digestive enzymes such as pancreatic lipase, trypsin, elastase, pancreatic amylase and the like.

Endocrine cells play a role of secreting pancreatic hormones, and it is known that glucagon is secreted from pancreatic α cells, insulin is secreted from pancreatic β cells, somatostatin is secreted from pancreatic δ cells, and pancreatic polypeptide (sometimes to be abbreviated as PP in the present specification) is secreted from PP cells. In recent years, it has been reported that ghrelin, which is a stomach-secreted hormone, is also secreted from pancreas.

Insulin plays an important role of promoting utilization of glucose, protein synthesis, and formation and storage of neutral fats, lowering blood glucose level, and maintaining blood glucose at a normal concentration. Pancreatic glucagon plays an important role, along with insulin, in a sugar metabolism regulatory mechanism, as a hyperglycemic hormone via hepatic glycogenolysis, gluconeogenesis action and the like. Somatostatin expresses an action by binding to a somatostatin receptor, and suppresses secretion of various hormones such as glucagon, insulin and the like in the pancreas. PP is a hormone secreted from the cells of islets of Langerhans in response to diet, known as a satiety factor, and reduces food ingestion and body weight gain. Ghrelin is known to stimulate food ingestion, and increase body weight gain by reducing fat oxidation.

Diabetes is a disease developed by insufficient insulin and loss of the function thereof, and difficult to cure once it is developed. Diabetes can be largely classified into two types of type I diabetes mellitus (insulin dependent diabetes) and type II diabetes mellitus (non-insulin dependent diabetes).

Type II diabetes mellitus is a chronic disease developed by resistance to insulin, which becomes problems in relation to lifestyle habits such as obesity due to overeating and inactivity, stress etc. Type II diabetes mellitus is often developed in middle-aged adults, and many of the diabetes patients are affected with this type diabetes.

Type I diabetes mellitus is a chronic disease caused by destruction of insulin-producing cells by autoimmune diseases, virus infection and the like to terminate secretion of insulin in the body. As a treatment method that can automatically control blood glucose level that continuously changes in the body and reduce burden on patients, pancreas transplantation or pancreatic islet transplantation is performed on patients with type I diabetes mellitus. While it is possible to achieve a normal blood glucose level by these treatment methods, the transplantation technique has not been sufficiently established, and the pancreas and pancreatic islet that can be transplanted are not sufficient. Moreover, to avoid immune rejection to a graft, the patients need to take an immunosuppressant for the entire life, and the problems of the risk of infection, side effects caused by immunosuppressant and the like still remain.

One of the treatment methods tried for type I diabetes mellitus is a method including reproducing an insulin-producing cell itself from the cells derived from the patient, and transplanting the cell into the body of the patient. According to this method, insulin can be produced in the body of the patient. In addition, since the cells are the patient's own cells, the method is also advantageous in terms of safety, since the problem of rejection can be resolved and the like.

Known methods for obtaining insulin-producing cells include a method of differentiating ES cells, a method of differentiating tissue stem cells of the pancreas of a patient, a method of isolating cells derived from the pancreatic duct epithelium of a patient out of body and differentiating the same and the like. Specifically, a method of inducing differentiation of pancreatic β cells from human ES cells by using activin and retinoic acid (RA) (patent document 1, non-patent documents 1-4), a method of inducing differentiation of glucagon-producing cells (α cells) from human ES cells (non-patent document 8), a method of inducing differentiation of pancreatic β cells from human iPS cells (non-patent documents 5-7), a method of efficiently inducing differentiation of insulin-producing cells, including introducing PDX1, which is known to be an important transcription factor involved in the development of the pancreas and also responsible for the development and function maintenance of insulin-producing cells, into ES cells, and cultivating the cells (patent document 2), and the like.

However, since the insulin-producing cells obtained by these methods show considerably low insulin production efficiency as compared to those of normal pancreatic β cells, the development of a method of efficiently obtaining insulin-producing cells that can be adopted for application of cell therapy is still required. Furthermore, it is desired to increase the number of obtainable cells to a practical level for the treatment of diabetes and the like.

DOCUMENT LIST

Patent Documents

[patent document 1] JP-A-2009-225661
[patent document 2] U.S. Pat. No. 7,534,608

Non-Patent Documents

[non-patent document 1] E. Kroon et al., "Pancreatic endoderm derived from human embryonic stem cells generates glucose-responsive insulin-secreting cells in vivo.", Nature Biotechnology (2008) Vol. 26, No. 4: 443-452
[non-patent document 2] K. A D'Amour et al., "Production of pancreatic hormone-expressing endocrine cells from human embryonic stem cells.", Nature Biotechnology (2006) Vol. 24, No. 11: 1392-1401
[non-patent document 3] W. Jiang, "In vitro derivation of functional insulin-producing cells from human embryonic stem cells.", Cell Research (2007) 17: 333-344

[non-patent document 4] J. H. Shim et al., "Directed differentiation of human embryonic stem cells towards a pancreatic cell fate.", Diabetologia (2007) 50:1228-1238

[non-patent document 5] R. Maehra et al., "Generation of pluripotent stem cells from patients with type 1 diabetes.", PNAS (2009), vol. 106, No. 37: 15768-15773

[non-patent document 6] MC. Nostro et al., "Stage-specific signaling through TGFbeta family members and WNT regulates patterning and pancreatic specification of human pluripotent stem cells.", Development (2011), 138: 861-871

[non-patent document 7] A. Rezania et al., "Production of functional glucagon-secreting alpha-cells from human embryonic stem cells.", Diabetes (2011), 60: 239-247

[non-patent document 8] T. Thatava et al., "Indolactam V/GLP-1-mediated differentiation of human iPS cells into glucose-responsive insulin-secreting progeny.", Gene Ther (2011), 18: 283-293

SUMMARY OF THE INVENTION

Problems to be Solved by the Invention

An object of the present invention is to provide a production method of pancreatic hormone-producing cells more suitable for the application of cell therapy, a medicament containing the pancreatic hormone-producing cells obtained by the production method, and a method of screening for a therapeutic drug for diabetes using the cells.

Means of Solving the Problems

The present inventors have conducted intensive studies in view of the above-mentioned problem, and found that pancreatic hormone-producing cells in a form more mimicking the pancreatogenesis (form maintaining a three-dimensional structure) can be produced from a stem cell, by serially changing the kind and combination of differentiation inducers and by cultivating in a suspension state after forming a cell mass from endodermal cells, and the like, which resulted in the completion of the present invention.

Accordingly, the present invention provides the following.

[1] A method of producing pancreatic hormone-producing cells, comprising subjecting stem cells to the following steps (1)-(6):
(1) a step of cultivating stem cells in a medium containing a Rho kinase inhibitor
(2) a step of cultivating the cells obtained in the aforementioned step (1) in a medium containing a GSK3 inhibitor
(3) a step of cultivating the cells obtained in the aforementioned step (2) in a medium containing GSK3 inhibitor and an activator of activin receptor-like kinase-4,7
(4) a step of forming a cell mass from the cells obtained in the aforementioned (3), and cultivating the cell mass in a suspension state in a medium
(5) a step of cultivating the cells obtained in the aforementioned step (4) in a medium containing a retinoic acid receptor agonist, an inhibitor of AMP-activated protein kinase and/or activin receptor-like kinase-2,3,6, an inhibitor of activin receptor-like kinase-4,5,7 and a cell growth factor
(6) a step of cultivating the cells obtained in the aforementioned step (5);

[2] the production method of the above-mentioned [1], wherein the activator of activin receptor-like kinase-4,7 in step (3) is activin;

[3] the production method of the above-mentioned [1] or [2], wherein the Rho kinase inhibitor in step (1) is (+)-(R)-trans-4-(1-aminoethyl)-N-(4-pyridyl)cyclohexanecarboxamide dihydrochloride;

[4] the production method of any of the above-mentioned [1] to [3], wherein the GSK3 inhibitor in steps (2) and (3) is (i) 6-[[2-[[4-(2,4-dichlorophenyl)-5-(4-methyl-1H-imidazol-2-yl)-2-pyrimidinyl]amino]ethyl]amino]nicotinonitrile and/or (ii) (2'Z,3'E)-6-bromoindirubin-3'-oxime;

[5] the production method of any of the above-mentioned [1] to [4], wherein the retinoic acid receptor agonist in step (5) is retinoic acid;

[6] the production method of any of the above-mentioned [1] to [5], wherein the inhibitor of AMP-activated protein kinase and/or activin receptor-like kinase-2,3,6 in step (5) is dorsomorphin;

[7] the production method of any of the above-mentioned [1] to [6], wherein the inhibitor of activin receptor-like kinase-4,5,7 in step (5) is 4-[4-(1,3-benzodioxol-5-yl)-5-(2-pyridinyl)-1H-imidazol-2-yl]-benzamide;

[8] the production method of any of the above-mentioned [1] to [7], wherein the cell growth factor in step (5) is basic fibroblast growth factor;

[9] the production method of any of the above-mentioned [1] to [8], wherein the steps (1)-(6) do not substantially use a feeder cell;

[10] the production method of any of the above-mentioned [1] to [7], wherein the medium in steps (1)-(6) does not substantially contain a serum;

[11] the production method of any of the above-mentioned [1] to [10], wherein the stem cells are induced pluripotent stem cells (iPS cells), embryonic stem cells (ES cells) or human somatic stem cells;

[12] the production method of any of the above-mentioned [1] to [11], wherein the pancreatic hormone-producing cells are any selected from the group consisting of insulin-producing cells, glucagon-producing cells, somatostatin-producing cells, pancreatic polypeptide (PP)-producing cells and ghrelin-producing cells;

[13] a method of producing pancreatic hormone-producing cells, comprising subjecting endodermal cells to the following steps (4') and (5'):
(4') a step of forming a cell mass from endodermal cells, and cultivating the cell mass in a suspension state in a medium
(5') a step of cultivating the cells obtained in the aforementioned step (4') in a medium containing a retinoic acid receptor agonist, an inhibitor of AMP-activated protein kinase and/or activin receptor-like kinase-2,3,6, an inhibitor of activin receptor-like kinase-4,5,7 and a cell growth factor;

[14] a medicament comprising pancreatic hormone-producing cells obtained by the production method of any one of the above-mentioned [1] to [13];

[15] a method of screening for a therapeutic drug for diabetes, comprising using the cells obtained by any one or more steps selected from the group consisting of the following steps (1)-(6):
(1) a step of cultivating stem cells in a medium containing a Rho kinase inhibitor
(2) a step of cultivating the cells obtained in the aforementioned step (1) in a medium containing a GSK3 inhibitor
(3) a step of cultivating the cells obtained in the aforementioned step (2) in a medium containing GSK3 inhibitor and an activator of activin receptor-like kinase-4,7
(4) a step of forming a cell mass from the cells obtained in the aforementioned (3), and cultivating the cell mass in a suspension state in a medium (5) a step of cultivating the cells obtained in the aforementioned step (4) in a medium containing a retinoic acid receptor agonist, an inhibitor of AMP-activated protein kinase and/or activin receptor-like kinase-2,3,6, an inhibitor of activin receptor-like kinase-4,5,7 and a cell growth factor
(6) a step of cultivating the cells obtained in the aforementioned step (5).

Effect of the Invention

According to the production method of the present invention, pancreatic hormone-producing cells in a form more mimicking the pancreatogenesis can be produced from stem cells. In addition, the cells obtained in one or more kinds of steps of the aforementioned step (1)-(6) can be used for screening for a compound useful for the prophylaxis and/or treatment of diseases caused by abnormal pancreatic hormone production and/or secretion such as diabetes and the like. Furthermore, since the cells of the present invention can be used for cell therapy for the treatment of such diseases and they maintain a three-dimensional structure, it is more suitable for the application to cell therapy even when compared to pancreatic hormone-producing cells obtained according to a conventional production method.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
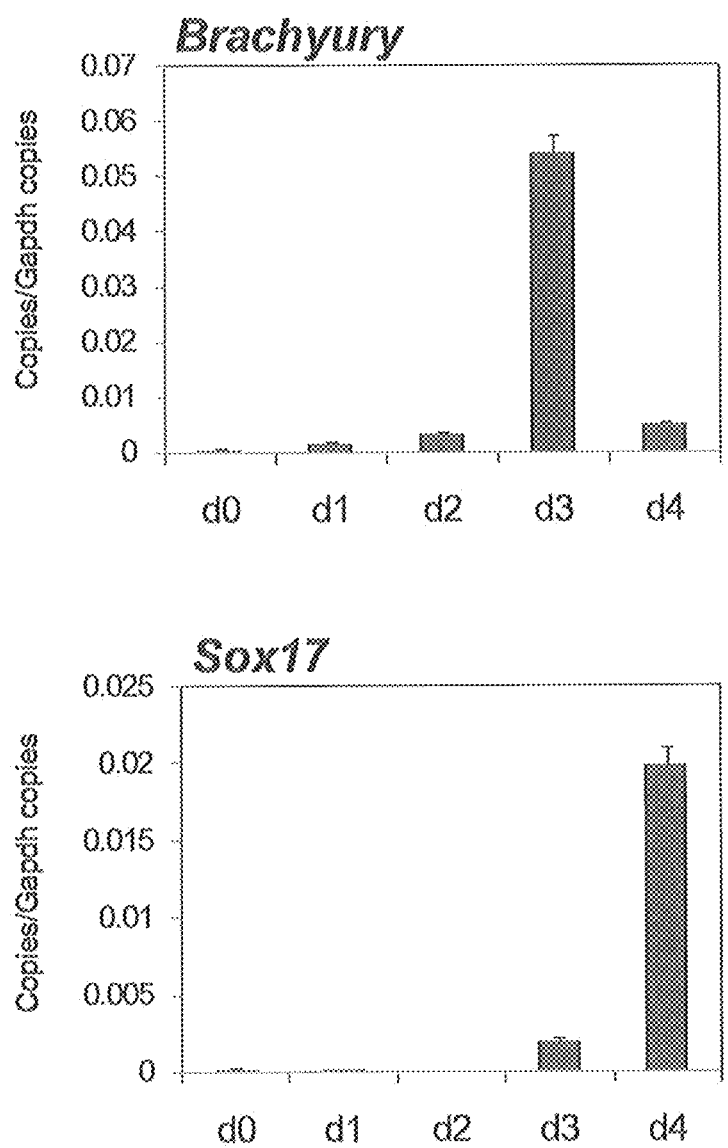
FIG. 1 shows the results obtained by initiating induction of differentiation from human iPS cells by using various factors, and measuring the expression of a primitive streak marker (Brachyury) and an endodermal marker (SOX17) every day for the first 4 days by quantitative RT-PCR. The expression levels of respective genes are shown as relative values to the expression level of a housekeeping gene GAPDH. On day 3 of culture, the expression level of Brachyury transiently increased, and the expression level of SOX17 remarkably increased on day 4.

The present invention is explained in the following. The terms used in the present specification mean those generally used in the field, unless particularly specified.

In the present invention, "pancreatic hormone-producing cells" means cells having an ability to produce pancreatic hormone. The pancreatic hormone-producing cells do not need to constantly produce pancreatic hormone, but only needs to have an ability to produce pancreatic hormone. Therefore, the amount of the pancreatic hormone to be produced is not particularly limited. Examples of the pancreatic hormone include insulin, glucagon, somatostatin, pancreatic polypeptide and ghrelin. Examples of the pancreatic hormone-producing cells include insulin-producing cells (synonymous with pancreatic β cells), glucagon-producing cells (synonymous with pancreatic α cells), somatostatin-producing cells (synonymous with pancreatic δ cells), pancreatic polypeptide (PP)-producing cells and ghrelin-producing cells. Of these, insulin-producing cells are preferable.

In the present invention, the "stem cells" means cells that can be cultivated in vitro, and can be differentiated into plural cellular lineages constituting the body. Specifically, embryonic stem cells (ES cells), pluripotent stem cells derived from primordial germ cells of embryo (EG cell: Proc Natl Acad Sci USA. 1998, 95:13726-31), testis-derived pluripotent stem cells (GS cells: Nature. 2008, 456: 344-9), somatic cell-derived induced pluripotent stem cells (induced pluripotent stem cells; iPS cells) and human somatic stem cells (tissue stem cells) can be mentioned. Preferred are iPS cells, ES cells and human somatic stem cells, and more preferred is iPS cells.

As the ES cells, ES cells derived from any warm-blooded animal, preferably mammal, can be used. Examples of the mammal include mouse, rat, guinea pig, hamster, rabbit, cat, dog, sheep, swine, bovine, horse, goat, monkey and human. Preferable examples of the cells derived from human.

Specific examples of the ES cells include ES cells of a mammal and the like, which is established by cultivating an early embryo before implantation, ES cells established by cultivating an early embryo prepared by nuclear transplantation of the nuclei of somatic cells, and ES cells obtained by altering the gene on the chromosome of such ES cells by genetic engineering. Each ES cell can be prepared by a method generally performed in the field or according to a known document.

ES cells of a mouse were established in 1981 by Evans et al. (Evans et al., 1981, Nature 292: 154-6) and Martin et al. (Martin G R. et al., 1981, Proc Natl Acad Sci 78: 7634-8) and can be purchased from, for example, Dainippon Sumitomo Pharma Co., Ltd. (Osaka, Japan).

ES cells of a human were established in 1998 by Thomson et al. (Thomson et al., Science, 1998, 282:1145-7), and can be obtained from WiCell Research Institute (web site: http://www.wicell.org/, Madison, Wis., USA), National Institute of Health, Kyoto University and the like and, for example, can be purchased from Cellartis AB (web site: http://www.cellartis.com/, Sweden).

As iPS cells, iPS cells derived from any warm-blooded animal, preferably mammal, can be used. Examples of the mammal include mouse, rat, guinea pig, hamster, rabbit, cat, dog, sheep, swine, bovine, horse, goat, monkey and human. Preferable examples include cells derived from human.

Specific examples of iPS cells include cells that have acquired multipotency like that of ES cells and were obtained by introducing plural genes into somatic cells such as skin cells and the like (e.g., iPS cells obtained by introducing Oct3/4 gene, Klf4 gene, c-Myc gene and Sox2 gene (Nat Biotechnol 2008; 26: 101-106)). Besides these, a method wherein transgenes are further reduced (Nature. 2008 Jul. 31; 454(7204):646-50), a method utilizing low-molecular-weight compounds (Cell Stem Cell. 2009 Jan. 9; 4(1):16-9, Cell Stem Cell. 2009 Nov. 6; 5(5):491-503), a method utilizing transcription factor proteins instead of a gene (Cell Stem Cell. 2009 May 8; 4(5):381-4) and the like can be mentioned.

Although technical improvements have been intensively made to the production methods of iPS cells, the basic property of the produced iPS cells, that is, they have multipotency, is equivalent regardless of the production methods, and therefore, all of such methods can be used for the production method of the present invention.

As the somatic stem cells, one derived from human can be used. Here, the somatic stem cells refers to cells capable of differentiation into pancreatic hormone-producing cells, for example, stem cells present in mesenchymal stem cells derived from bone marrow and fat and stem cells present in the pancreas.

Using the method of the present invention, pancreatic hormone-producing cells can be produced from various stem cell lines such as human iPS cell line which vary in production methods.

1. Production Method of Pancreatic Hormone-Producing Cells

The production method of the present invention includes a method of producing pancreatic hormone-producing cells from stem cells. The production method of the present invention also includes a method of inducing differentiation of cells in a less differentiated state (stem cells) into a more differentiated state (pancreatic hormone-producing cells).

The production method of the present invention includes the following steps (1)-(6).
(1) a step of cultivating stem cells in a medium containing a Rho kinase inhibitor
(2) a step of cultivating the cells obtained in the aforementioned step (1) in a medium containing a GSK3 inhibitor
(3) a step of cultivating the cells obtained in the aforementioned step (2) in a medium containing GSK3 inhibitor and an activator of activin receptor-like kinase-4,7
(4) a step of forming a cell mass from the cells obtained in the aforementioned (3), and cultivating the cell mass in a suspension state in a medium
(5) a step of cultivating the cells obtained in the aforementioned step (4) in a medium containing a retinoic acid receptor agonist, an inhibitor of AMP-activated protein kinase and/or activin receptor-like kinase-2,3,6, an inhibitor of activin receptor-like kinase-4,5,7 and a cell growth factor
(6) a step of cultivating the cells obtained in the aforementioned step (5)

Step (1): a Step of Cultivating Stem Cells in a Medium Containing a Rho Kinase Inhibitor The step corresponds to a preliminary step before the below-mentioned step (2) initiating the induction of differentiation of the stem cells into pancreatic hormone-producing cells, that is, the stage of preculture (seeding) of stem cells.

The stem cells in this step may be obtained by co-culture with feeder cells or a feeder cell extract. Here, the feeder cell means a cell that provides, by co-culture, an environment in which other kinds of cells can grow.

While the stem cells in this step may be any of dispersed cells and non-dispersed cells, dispersed cells are desirable.

Examples of the dispersed cells include singulated cells, and cells forming a cell mass consisting of several cells (typically about 2-500, 20-200 or 50-100 cells) [as explained in the below-mentioned step (4), the cell mass means a condition of forming a mass by adhering plural cells each other and the like], which is desirably a cell mass in this step.

A dispersed cell can be prepared by a method known per se. Examples of such method include a treatment with a chelating agent (e.g., EDTA), an enzyme (e.g., trypsin, collagenase) and the like, and handlings such as mechanical dispersion (e.g., pipetting) and the like.

The dispersed cells can be non-adherent cells [non-adherent cells mean cells in the state free of adhesion to culture vessel or a substrate], or adherent cells [adherent cells mean cells in an adhesion state to culture vessel or a substrate].

In this step, it is desirable to, after removing the feeder cells or the feeder cell extract (e.g., removing by placing in a centrifuge tube, standing for 2-10 min and then removing the supernatant), cultivate the cells in the below-mentioned medium containing Rho kinase inhibitor (that is, initiate induction of differentiation without using feeder cells at the seeding and thereafter).

The Rho kinase inhibitor means a substance that inhibits the activity of Rho kinase.

The Rho kinase is one kind of small GTP-binding protein (small G protein) contained in the category of GTPase, which is a degrading enzyme of GTP (guanosine triphosphate), and has a serine/threonine kinase domain at the amino terminal, a coiled coil region in the central part and a Rho interactiing domain at the carboxy terminal (Amano et al., Exp. Cell. Res., 261, 44-51 (2000)).

Examples of the Rho kinase inhibitor to be used in this step include 1-(5-isoquinolinesulfonyl)-2-methylpiperazine (H-7), 1-(5-isoquinolinesulfonyl)-3-methylpiperazine (isoH-7), N-2-(methylamino)ethyl-5-isoquinolinesulfonamide dihydrochloride (H-8), N-(2-aminoethyl)-5-isoquinolinesulfonamide dihydrochloride (H-9), N-[2-p-bromocinnamylamino)ethyl]-5-isoquinolinesulfonamide dihydrochloride (H-89), N-(2-guanidinoethyl)-5-isoquinolinesulfonamide hydrochloride (HA-1004), 1-(5-isoquinolinesulfonyl)homopiperazine dihydrochloride (Fasudil/HA-1077), (S)-(+)-2-methyl-4-glycyl-1-(4-methylisoquinolinyl-5-sulfonyl)homopiperidine dihydrochloride (H-1152), and (+)-(R)-trans-4-(1-aminoethyl)-N-(4-pyridyl)cyclohexanamide dihydrochloride (Y-27632).

These are all commercially available (e.g., available for purchase from SIGMA and Wako Pure Chemical Industries, Ltd.). Of these, Y-27632 is particularly preferable.

In this step, single and any combination of two or more kinds of Rho kinase inhibitors can be used.

In this step, the stem cell is cultured in a medium containing Rho kinase inhibitor.

While the concentration of the Rho kinase inhibitor in the medium is not particularly limited as long as it can achieve a desired effect such as improvement of survival rate of stem cells and the like, it is generally 0.01-1000 μM, preferably 0.1-100 μM, particularly preferably 1.0-50 μM. When Y-27632 is used as Rho kinase inhibitor, the concentration preferably used is about 1.0-about 30 μM, more preferably about 2.0-about 20 μM. When Fasudil/HA1077 is used as Rho kinase inhibitor, the concentration may be about 2-fold compared to the above-mentioned concentration of Y-27632.

When plural kinds of Rho kinase inhibitors are used in combination, each inhibitor is used at a concentration appropriately increased or decreased based on the above-mentioned concentration range.

The culture time in a medium containing a Rho kinase inhibitor is not particularly limited as long as it can achieve a desired effect such as improvement of survival rate of stem cells and the like. For example, when the stem cell is human iPS cell, human iPS cells are dispersed and cultured in a medium containing Rho kinase inhibitor for about 12 hr or longer (e.g., 12-72 hr), whereby the desired effect can be sufficiently obtained.

The density of the stem cells in the medium containing Rho kinase inhibitor is not particularly limited as long as it can achieve a desired effect such as improvement of survival rate of stem cells and the like. It is preferably about $1.0 \times 10^1$-$1.0 \times 10^7$ cells/ml, more preferably about $1.0 \times 10^2$-$1.0 \times 10^7$ cells/ml, further more preferably about $1.0 \times 10^3$-$1.0 \times 10^7$ cells/ml, most preferably about $3.0 \times 10^4$-$1.0 \times 10^6$ cells/ml.

The medium to be used in this step is not particularly limited as long as it contains Rho kinase inhibitor, and is generally a medium used for cultivating stem cells added with Rho kinase inhibitor (hereinafter to be also referred to as a basal medium for convenience).

As the basal medium to be used in this step, a medium for primate ES/iPS cells (ReproCELL medium), BME medium, BGJb medium, CMRL 1066 medium, Glasgow MEM medium, Improved MEM Zinc Option medium, IMDM medium, Medium 199 medium, Eagle MEM medium, αMEM medium, DMEM medium, ham medium, RPMI 1640 medium, Fischer's medium, a mixture of two or more kinds of media optionally selected from these media and the like can be used. The medium is not particularly limited as long as it can be used for culturing animal cells. In this step, a medium for primate ES cell (ReproCELL medium) is particularly desirably used.

These media can be purchased from ReproCELL Inc., Invitrogen, SIGMA, COSMO BIO Co., Ltd. and the like.

As the medium to be used in this step, a medium substantially free of serum and/or serum extract is preferable, and a serum-free medium is more preferable.

In the present specification, substantially free of serum means that the content of the serum is less than about 1 volume %, preferably less than about 0.1 volume %, more preferably less than about 0.01 volume %. A serum-free medium means a basal medium free of unadjusted or unpurified serum, and a medium mixed with purified blood-derived component or animal tissue-derived component (e.g., growth factor) is considered to fall under a serum-free medium.

The medium to be used in this step may also contain serum replacements. Examples of the serum replacement include albumin (e.g., lipid rich albumin), transferrin, fatty acid, collagen precursor, trace element (e.g., zinc, selenium), B-27 supplement, N2 supplement, knockout serum replacement, 2-mercaptoethanol, 3'-thiolglycerol, or equivalents thereof. A knockout serum replacement can be purchased from Invitrogen. Other serum replacements can be purchased from Invitrogen, SIGMA, Wako Pure Chemical Industries, Ltd., Dainippon Sumitomo Pharma Co., Ltd. and the like.

The concentration in the medium, of B-27 supplement when used, is 0.01-10 wt %, preferably 0.1-2 wt %.

In this step, it is preferable to not substantially use feeder cells and/or a feeder cell extract. That is, the medium to be used in this step is preferably a medium substantially free of feeder cells and/or a feeder cell extract, more preferably a medium completely free of feeder cells and/or a feeder cell extract.

In the present specification, substantially free of feeder cells and/or a feeder cell extract means that the content of the feeder cells and/or the feeder cell extract in the medium is less than about 5 volume %, preferably less than about 1 volume %, more preferably less than about 0.01 volume %.

When the feeder cells and/or the feeder cell extract are/is not substantially used in this step, the pancreatic hormone-producing cells produced by the production method of the present invention are less contaminated with the causative substance of rejection (e.g., animal-derived cells).

The culture in this step is generally performed using culture vessels. While such culture vessel is not particularly limited as long as stem cells can be cultured, cell-adhesive culture vessel is desirably used for performing adhesion culture, and cell non-adhesive culture vessel is desirably used for performing floating culture. Examples of the culture vessel include flask, tissue culture flask, dish, petri dish, tissue culture dish, multidish, microplate, microwell plate, multiplate, multiwell plate, micro slide, chamber slide, schale, tube, tray, culture bag and roller bottle. Cell-adhesive culture vessel is a culture vessel coated with any cell supportive substrate such as extracellular matrix (ECM) and the like, so as to improve the adhesiveness of the cells to the surface of the culture vessel.

Examples of the culture vessel for adhesion culture include dish, flask, microplate, cell culture sheet and the like. These culture vessels may be imparted with hydrophilicity to improve adhesiveness to the cell, or coated with cell supporting substrates such as collagen, gelatin, poly-L-lysine, poly-D-lysine, laminin, fibronectin and the like. The cell culture sheet refers to a support aiming to cultivate cells in a sheet-like form and is commercially available from, for example, OptiCell (Nunc).

As the cell supporting substrate in this step, preferred are Type I-collagen, BD Matrigel (Nippon Becton Dickinson Company, Ltd.), fibronectin (Invitrogen) and the like, more preferred are BD Matrigel and fibronectin, and further preferred is fibronectin.

Examples of the culture vessel for floating culture include dish, flask, microplate, tube, roller bottle and the like. These culture vessels may be manufactured from hydrophobic material, or coated with material preventing adsorption of a cell and protein such as hydrogel, lipid and the like. A culture vessel having a U- or V-shaped bottom is desirably used to efficiently form cellular aggregates.

Other culture conditions can be appropriately determined. For example, the culture temperature is not particularly limited as long as it is suitable for the culture of stem cells to be used, and may be about 30-40° C., preferably about 37° C. The $CO_2$ concentration can be about 1-10%, preferably about 2-5%. The oxygen partial pressure can be 1-10%.

Step (2): a Step of Cultivating the Cells Obtained in the Aforementioned Step (1) in a Medium Containing GSK3 Inhibitor This step is performed following the aforementioned step (1), and corresponds to a step of inducing differentiation of stem cells into endodermal cells together with the below-mentioned step (3).

GSK3 (glycogen synthase kinase 3), which is a serine/threonine protein kinase, is involved in many signal pathways relating to the production of glycogen and apoptosis, maintenance of stem cells and the like. GSK3 includes isoforms of GSK3α and GSK3β which are encoded by different genes and have high homology at an amino acid sequence level. It is known that GSK3 is also involved in Wnt signaling, and inhibition of GSK3 activates Wnt signal.

Examples of the GSK3 inhibitor include GSK3α inhibitor and GSK3β inhibitor. In this step, GSK3α inhibitor is desirable.

Specific examples of the GSK3 inhibitor include CHIR98014 (2-[[2-[(5-nitro-6-aminopyridin-2-yl)amino] ethyl]amino]-4-(2,4-dichlorophenyl)-5-(1H-imidazol-1-yl) pyrimidine), CHIR99021, Kenpaullone, AR-AO144-18, TDZD-8 (4-benzyl-2-methyl-1,2,4-thiadiazolidine-3,5-dione), SB216763 (3-(2,4-dichlorophenyl)-4-(1-methyl-1H-indol-3-yl)-1H-pyrrole-2,5-dione), BIO, TWS-119 (3-[6-(3-aminophenyl)-7H-pyrrolo[2,3-d]pyrimidin-4-yloxy] phenol), SB415286 (2-(3-chloro-4-hydroxyphenylamino)-3-(2-nitrophenyl) maleimide [2-[2,5-dihydro-4-[(3-chloro-4-hydroxyphenyl)amino]-2,5-dioxo-1H-pyrrol-3-yl]phenyl] oxylatoiminium) and the like. These can be purchased from Axon Medchem BV, Wako Pure Chemical Industries, Ltd., Enzo Life Sciences, Inc., Merck Biosciences, Tocris bioscience, Stemgent, Sigma and the like.

In addition, antisense oligonucleotide, siRNA and the like for GSK3 mRNA can also be used as GSK3 inhibitor. All of these are commercially available or can be synthesized according to published documents.

A method of using Wnt-3A peptide for inducing differentiation of stem cells into endodermal cells is known (non-patent documents 1, 2 and 5). In this step, superior operability, reproducibility and selectivity can be provided by using GSK3 inhibitor, which is low-molecular-weight compound.

The GSK3 inhibitor is preferably CHIR99021 (6-[[2-[[4-(2,4-dichlorophenyl)-5-(4-methyl-1H-imidazol-2-yl)-2-pyrimidinyl]amino]ethyl]amino]nicotinonitrile) or BIO ((2'Z, 3'E)-6-bromoindirubin-3'-oxime).

In this step, single and any combinations of two or more kinds of GSK3 inhibitors can be used.

While the concentration of GSK3 inhibitor in a medium is appropriately determined according to the kind of the inhibitor to be used, it is generally 0.01-100 μM, preferably 0.1-10 μM. When CHIR99021 is used, the concentration is generally 0.1-20 μM, preferably 1-5 μM, and when BIO is used, the concentration is generally 0.01-5 μM, preferably 0.1-2 μM.

When plural kinds of GSK3 inhibitors are used in combination, the amounts of each inhibitor are appropriately increased or decreased based on the above-mentioned concentration range.

The medium to be used in this step is not particularly limited as long as it contains GSK3 inhibitor, and is generally, a medium used for cultivating stem cells (basal medium), which is added with GSK3 inhibitor.

The above-mentioned basal medium includes BME medium, BGJb medium, CMRL 1066 medium, Glasgow MEM medium, Improved MEM Zinc Option medium, IMDM medium, Medium 199 medium, Eagle MEM medium, αMEM medium, DMEM medium, serum-free DMEM/F12 medium, ham medium, RPMI 1640 medium, Fischer's medium, and mixed medium thereof and the like. The basal medium to be used in this step is not particularly limited as long as it can be used for culture of animal cells. These basal media can be purchased from Invitrogen, SIGMA, Wako Pure Chemical Industries, Ltd., Dainippon Sumitomo Pharma Co., Ltd. and the like.

The basal medium to be used in this step is preferably serum-free DMEM/F12 medium, RPMI 1640 medium and Improved MEM Zinc Option medium, particularly preferably serum-free DMEM/F12 medium.

As the medium to be used in this step, a medium substantially free of serum and/or serum extract is preferable, and a serum-free medium is more preferable.

In this step, it is preferable not to substantially use feeder cells and/or a feeder cell extract, and more preferable not to use feeder cells and/or a feeder cell extract at all.

When feeder cells and a feeder cell extract are not substantially used, the pancreatic hormone-producing cell produced by the production method of the present invention contains less amount of a substance (e.g., animal-derived cells) causing rejection.

The medium to be used in this step may also contain a serum replacement.

Examples of the serum replacement include albumin, transferrin, fatty acid, collagen precursor, trace element (e.g., zinc, selenium), B-27 supplement, N2 supplement, knockout serum replacement, 2-mercaptoethanol, 3'-thiolglycerol, or equivalents thereof. The serum replacement to be used in this step is preferably B-27 supplement.

The concentration in the medium of the B-27 supplement when used is 0.01-10 wt %, preferably 0.1-2 wt %. These serum replacements can be purchased from Invitrogen, SIGMA, Wako Pure Chemical Industries, Ltd., Dainippon Sumitomo Pharma Co., Ltd. and the like.

While the culture temperature in this step is not particularly limited as long as it is suitable for culture of stem cells to be used, it is about 30-40° C., preferably about 37° C.

The culture time is 6-144 hr, preferably 12-72 hr, at a culture temperature of about 37° C. The culture in this step is generally performed in an incubator aerated with about 1-10%, preferably 5%, of $CO_2$.

Step (3): a Step of Cultivating the Cells Obtained in the Aforementioned Step (2) in a Medium Containing GSK3 Inhibitor and an Activator of Activin Receptor-Like Kinase-4,7

This step is performed following the aforementioned step (2), and corresponds to a step for completing the induction of differentiation of stem cells into endodermal cells.

The activator of activin receptor-like kinase (ALK)-4,7 used in this step is selected from the substances having an activation action on ALK-4 and/or ALK-7.

Examples of the activator of activin receptor-like kinase-4,7 used in this step include activin, Nodal and Myostatin. All these activators are commercially available. Of these, activin is preferable as the activator of activin receptor-like kinase-4,7 used in this step.

The above-mentioned activin is a 24 kD peptidic cell proliferation and differentiation factor belonging to the TGFβ (transforming growth factor β) family, wherein two β subunits constitute a dimer via an SS bond (Ling, N., et al., (1986) Nature 321, 779-782; Vale, W., et al., (1986) Nature 321, 776-779). In the present invention, any of activins A, B, C, D and AB, and activin derived from any animal such as human, mouse and the like can be used, and these are commercially available. Of these, activin A is particularly preferably used. An activin derived from the same animal species as the stem cells to be used for differentiation is preferably used. For example, stem cells derived from human are used as a starting material, human activin A is preferably used.

While the concentration of an activator of activin receptor-like kinase-4,7 in the medium in this step is appropriately determined according to the kind of the activator of activin receptor-like kinase-4,7, the concentration of human activin A used as an activator of activin receptor-like kinase-4,7 is generally 0.1-200 ng/ml, preferably 5-150 ng/ml, particularly preferably 10-100 ng/ml.

In this step, single and any combination of two or more kinds of activators of activin receptor-like kinase-4,7 can be used. When plural kinds of activators are used in combination, the amounts of each activator are appropriately increased or decreased based on the above-mentioned concentration range. In this step, an activator of activin receptor-like kinase-4,7 is added to a medium together with GSK3 inhibitor. When stem cells are cultured in the presence of activin and GSK3 inhibitor, the cells can be differentiated into endodermal cells more preferably.

Examples of the GSK3 inhibitor to be used in this step include GSK3α inhibitor and GSK3β inhibitor. As the GSK3 inhibitor to be used in this step, a GSK3α inhibitor is preferable.

Specific examples of the GSK3 inhibitor to be used in this step include those similar to the GSK3 inhibitors exemplified in the aforementioned step (2). Also in this step, CHIR99021 or BIO, which is a GSK3 inhibitor, is preferably used. While the concentration of the GSK3 inhibitor in the medium is appropriately determined according to the kind of the inhibitor to be used, the concentration of CHIR99021 when used is generally 0.1-20 μM, preferably 1-5 μM, and the concentration of BIO when used is generally 0.01-5 μM, preferably 0.1-2 μM.

In this step, single and any combination of two or more kinds of GSK3 inhibitors can be used. When plural kinds of inhibitors are used in combination, the amounts of each inhibitor are appropriately increased or decreased based on the above-mentioned concentration range.

In this step, an activator of activin receptor-like kinase-4,7 and GSK3 inhibitor may be simultaneously added to the medium, or may be individually added to the medium in a staggered manner, as long as differentiation of stem cells into endodermal cells can be induced. It is convenient and preferable that an activator of activin receptor-like kinase-4,7 and GSK3 inhibitor are simultaneously added to a medium.

The medium to be used in this step is produced by adding activator of activin receptor-like kinase-4,7 and GSK3 inhibitor to the basal medium exemplified in the aforementioned step (2).

The medium to be used in this step may be produced using the same kind of basal medium as that used in the aforementioned step (2), or using a different kind of basal medium. Preferred is a medium produced using the same kind of basal medium (e.g., serum-free DMEM/F12 medium).

The basal medium to be used in this step is preferably serum-free DMEM/F12 medium, RPMI 1640 medium and Improved MEM Zinc Option medium, particularly preferably serum-free DMEM/F12 medium.

In this step, it is preferable not to substantially use feeder cells and/or a feeder cell extract, and more preferable not to use a feeder cells and/or a feeder cell extract at all.

As the medium to be used in this step, a medium substantially free of serum and/or serum extract is preferable, and a serum-free medium is more preferable.

When feeder cells and a feeder cell extract are not substantially used, the pancreatic hormone-producing cell produced by the production method of the present invention contains less amount of substances (e.g., animal-derived cells) causing rejection.

The medium to be used in this step may also contain serum replacement.

Examples of the serum replacement include albumin, transferrin, fatty acid, collagen precursor, trace element (e.g., zinc, selenium), B-27 supplement, N2 supplement, knockout serum replacement, 2-mercaptoethanol, 3'-thiolglycerol, or equivalents thereof, with preference given to B-27 supplement. The concentration in the medium of the B-27 supplement when used is 0.01-10 wt %, preferably 0.1-2 wt %.

While the culture temperature in this step is not particularly limited as long as it is suitable for culture of cells to be used, it is about 30-40° C., preferably about 37° C.

The culture time is 6-288 hr, preferably 12-124 hr, at culture temperature of about 37° C. The culture in this step is generally performed in an incubator aerated with about 1-10%, preferably 5%, of $CO_2$.

In this step, induction of differentiation of stem cells into endodermal cells is confirmed using endoderm markers. Specifically, the confirmation can be performed by evaluating the presence or absence of expression of a protein or gene that is specifically expressed in endodermal cells (endoderm marker). The expression of protein can be evaluated by a method utilizing an antigen-antibody reaction and the like, and the expression of gene can be evaluated by a method utilizing RT-PCR and the like. Examples of the marker include SOX17 (sex determining region Y), Goosecoid (goosecoid homeobox), CXCR4 (chemokine (C—X—C motif) receptor 4) and FOXA2 (forkhead box A2).

Step (4): a Step of Forming a Cell Mass (Sphere) from the Cells Obtained in the Aforementioned (3), and Cultivating the Cell Mass in a Suspension State in a Medium In this step, the cells obtained in the aforementioned step (3), that have been differentiated into endodermal cells, namely, endodermal cells, form a cell mass, and the cell mass is cultivated in a suspension state in a medium (re-seeding step).

In the present specification, the cell mass refers to a state where plural cells are adhered and the like to each other to form single mass (e.g., state wherein 10 or more cells are adhered to each other), and is a concept opposed to an isolated cell and nearly isolated cell. The isolated cell refers to one cell in an independent state without adhering to other cell. The nearly isolated cell refers to a group of several cells adhered to 1 or 2 other cells, or assembled by a weak adhesion force that allows easy separation from each other.

In this step, the cell mass refers to a state where plural (e.g., 10 or more) cells (endodermal cells) obtained in the aforementioned step (3) adhere to each other to form one mass.

The cell mass, isolated cells and nearly isolated cells may be distinguished by the number of the gathered cells (e.g., cell mass when 3 or more cells gather), or may be distinguished by the area of one assembly of cells in an enlarged planar image of cell suspension under an optical microscope and the like.

For example, when the size (radius) of a cell is about 10 μm, the sectional area thereof is about 300 μm$^2$. Therefore, for example, when the area of a region forming one assembly of cell is less than 300 μm$^2$, it may be recognized as isolated cells or nearly isolates cells, and when it is larger than 900 μm$^2$ (that is, corresponds to 3 cells), it may be recognized as a cell mass. When 10 or more cells are adhered to each other to form a cell mass, the sectional area thereof is assumed to be 3000 μm$^2$ or more.

In the present specification, to culture in a suspension state means cultivating in a medium under non-adhesive conditions. The culture under the non-adhesive conditions means culture in a state free of adhesion to culture vessel or substrate (e.g., using a non-adhesive multi-well plate).

The culture under the non-adhesive conditions can be performed by a method known per se. Examples of such method include a method including applying a hydrophilic substance proteoglycan such as poly(hydroxyethylmethacrylate) and the like to the surface of culture vessel to inhibit cellular adhesion to substrate (Cell Struct Funct, 13, 179 (1988)), and a method including applying a synthetic polymer compound, which dissolves in a culture medium by cooling, to the surface of culture vessel, allowing cells to adhere thereto, and dissolving the synthetic polymer compound by cooling the culture vessel to form cellular sheet (Bio Technology, 8, 854 (1990)). These methods can be improved as necessary. For example, to prevent loss of cells during exchange of culture media, it is possible to once subject a culture vessel to a centrifugation operation to forcibly attached cell mass to the surface of the culture vessel and change the culture medium, or to transfer a culture medium including cells into centrifuge tube, precipitate the cells by centrifugation operation and exchange the culture medium in supernatant.

In this step, before forming a cell mass, a protein digestion enzyme may be added to the cells obtained in the aforementioned step (3) (endodermal cells) to separate each cell to be singulated cells.

Examples of the usable protein digestion enzyme include, but are not limited to, trypsin, collagenase, papain, dispase, Accutase (Invitrogen, trade name) and the like. These protein digestion enzymes are typically used in the form of a trypsin-EDTA solution (e.g., 0.25% trypsin-1 mM EDTA) by adding EDTA to chelate $Ca^{2+}$ and $Mg^{2+}$, which are inhibitors of digestion enzymes.

In this step, for example, a cell mass can be prepared as follows from the cells obtained in the aforementioned step (3).

That is, the cells obtained in the aforementioned step (3) are subjected to floating culture in a suitable medium on a culture vessel. For example, when 96-well round-bottom dish is used as a low adhesive culture vessel, 20,000-400,000 cells are plated per well, and cultivated in a suitable medium at 37° C. for about 6 hr-about 10 days, preferably about 6 hr-about 2 days, more preferably 1 day, with or without transferring formed aggregates into a low adhesive 6 cm-dish and the like. Examples of the low adhesive culture vessel include those generally used in this technical field and treated to be low adhesive. Examples of the culture vessel include culture dish, culture flask, apparatus for rotary culture (spinner flask etc.) and the like, specifically spheroid plate. As the treatment to be low adhesive, a treatment to suppress adhesion of protein and cells by forming a covalent bond (coating) of hydrogel is used.

To be specific, in this step, the cells obtained in the aforementioned step (3) are plated on 96-well spheroid plate at, for example, a density of $2 \times 10^4$ cells per well, and cultivated under conditions of 37° C. and 5% $CO_2$ for 1 day in an Improved MEM Zinc Option medium added with 1% B-27 supplement.

In this step, the cell mass obtained as mentioned above is cultivated in suspension state in a medium. The culture in suspension state means, as mentioned above, culture in a state free of adhesion to culture vessel or substrate (e.g., using a non-adhesive multi-well plate).

Examples of the medium to be used in this step (that is, medium for re-plating) include the basal media exemplified in the aforementioned step (2). The medium to be used in this step may be prepared by using the same kind of a basal medium as the above-mentioned steps (2)-(3), or using a different basal medium. Since induction of differentiation into pancreatic hormone-producing cells can be performed more efficiently, Improved MEM Zinc Option medium (Invitrogen) is preferably used as the basal medium for this step. The medium can also be prepared according to a known document (Richter A. et al., National Cancer (1972) 49, 1705).

The medium to be used in this step may also contain serum replacement. Examples of the serum replacement include albumin, transferrin, fatty acid, collagen precursor, trace element (e.g., zinc, selenium), B-27 supplement, N2 supplement, knockout serum replacement, 2-mercaptoethanol, 3'-thiolglycerol, or equivalents thereof. As the serum replacement to be used in this step, B-27 supplement is preferable.

In this step, an Improved MEM Zinc Option medium (Invitrogen) added with B-27 supplement is particularly preferably used. In the medium, the concentration of the B-27 supplement is 0.01-10 wt %, preferably 0.1-2 wt %.

In this step, it is preferable not to substantially use feeder cells and/or a feeder cell extract, and more preferable not to use feeder cells and/or a feeder cell extract at all.

When feeder cells and a feeder cell extract are not substantially used, a substance (e.g., animal-derived cells) causing rejection is contained in a less amount.

As the medium to be used in this step, a medium substantially free of serum and/or serum extract is preferable, and a serum-free medium is more preferable.

While the culture temperature is not particularly limited as long as it is suitable for culture of cells to be used, it is about 30-40° C., preferably about 37° C.

The culture time is 6-360 hr, preferably about 1 day-about 12 days, more preferably about 8 days.

When a cell mass is formed in a suspension state, after formation of the cell mass, the cell mass can also be subjected to step (5) without subjecting to floating culture. In this case, the formed cell mass may be cultured in a suspension state for 0-48 hr, preferably 0-24 hr, before was performing step (5).

The culture in this step is generally performed in an incubator aerated with about 1-10%, preferably 5%, of $CO_2$.

To be specific, in this step, the cells obtained in the aforementioned step (3) are plated on a 96-well spheroid plate, for example, at a density of $2 \times 10^4$ cells per well, and cultivated under conditions of 37° C. and 5% $CO_2$ for 1 day in an Improved MEM Zinc Option medium added with 1% B-27 supplement.

In this step (4), pancreatic hormone-producing cells can also be produced using, as a starting material, endodermal cells other than those obtained by the aforementioned steps (1)-(3). Therefore, the present invention also provides, by this step (4), a production method of pancreatic hormone-producing cells using endodermal cells as a starting material, that is, a production method of pancreatic hormone-producing cells, comprising forming a cell mass from endodermal cells, and cultivating the cell mass in a suspension state in a medium (sometimes to be abbreviated as production method 2 of the present invention in the present specification).

The production method of pancreatic hormone-producing cells using, as a starting material, endodermal cells other than those obtained by the aforementioned steps (1)-(3) can also be performed in the same manner as in step (4) of the production method of pancreatic hormone-producing cells using the cells obtained in the aforementioned step (3) as a starting material.

To be specific, the production method 2 of the present invention is characterized by subjecting endodermal cells to the following steps (4') and (5').

(4') a step of forming a cell mass from endodermal cells, and cultivating the cell mass in a suspension state in a medium (5') a step of cultivating the cells obtained in the aforementioned step (4') in a medium containing retinoic acid receptor agonist, inhibitor of AMP-activated protein kinase and/or activin receptor-like kinase-2,3,6, inhibitor of activin receptor-like kinase-4,5,7 and cell growth factor The step (4') can be performed in the same manner as in the above-mentioned step (4), and step (5') can be performed in the same manner as in the above-mentioned step (5).

Pancreatic hormone-producing cells in a form more mimicking the pancreatogenesis can be produced by this step, more preferably, the aforementioned step (1)-(3) followed by this step (4). Since these cells form three-dimensional structure of a cell mass, it is considered to be closer to the state in the body and more functional than the cells cultured in single layer. Furthermore, due to the three-dimensional structure, these cells are considered to be more suitable for application to cell therapy as compared to pancreatic hormone-producing cells obtained by conventional production methods.

Step (5): a Step of Cultivating the Cells Obtained in the Aforementioned Step (4) in a Medium Containing Retinoic Acid Receptor Agonist, Inhibitor of AMP-Activated Protein Kinase and/or Activin Receptor-Like Kinase-2,3,6, Inhibitor of Activin Receptor-Like Kinase-4,5,7 and Cell Growth Factor This step corresponds to a step of inducing differentiation of the cell obtained in the aforementioned step (4), namely, endodermal cells cultured in a suspension state into progenitor cells of pancreatic hormone-producing cells.

The retinoic acid receptor (RAR) agonist to be used in this step may be a naturally-occurring retinoid, or synthesized retinoid, a retinoic acid receptor agonist compound free of retinoid skeleton, or a naturally-occurring substance having an equivalent activity. Examples of the naturally-occurring retinoid include retinoic acid (stereoisomers of all-trans retinoic acid (all-trans RA) and 9-cis-retinoic acid (9-cis RA) are known). A synthesized retinoid is known in this field (U.S. Pat. No. 5,234,926, U.S. Pat. No. 4,326,055 etc.). Examples of the retinoic acid receptor agonist compound free of retinoid skeleton include Am80, TTNPB and AC55649. Examples of the naturally-occurring substance include honokiol and magnolol (Annual Report of Research Institute for Biological Function 9:55-61, 2009). The RAR agonist to be used in this step is preferably retinoic acid. While the concentration of RAR agonist in the medium is appropriately determined according to the kind of the RAR agonist to be used, the concentration of retinoic acid when used is generally 0.1-100 μM, preferably 0.5-10 μM.

The inhibitor of AMP-activated protein kinase and/or activin receptor-like kinase-2,3,6 to be used in this step is selected from the group consisting of compounds having inhibitory activity on AMP-activated protein kinase (AMPK), compounds having inhibitory activity on activin receptor-like kinase (ALK)-2,3,6, and compounds having inhibitory activity on AMP-activated protein kinase and inhibitory activity on activin receptor-like kinase-2,3,6 in combination.

Examples of the compound having AMPK inhibitory activity include dorsomorphin (6-[4-(2-piperidin-1-ylethoxy)phenyl]-3-pyridin-4-ylpyrazolo[1,5-a]pyrimidine), araA (adenine-9-β-d-arabino furanoside), C75 and the like. The activin receptor-like kinase (ALK) has been classified into some types and ALK-2,3,6 is known as a BMP type I receptor kinase, and the below-mentioned ALK-4,5,7 is known as a TGF-β, superfamily type I receptor kinase. As compounds having ALK-2,3,6 inhibitory activity, dorsomorphin, LDN-193189 (6-(4-piperazinophenyl)-3-(quinolin-4-yl)pyrazolo [1,5-a]pyrimidine) and the like can be mentioned. Dorsomorphin has both AMPK inhibitory activity and ALK-2,3,6 inhibitory activity. As an inhibitor of AMP-activated protein kinase and/or activin receptor-like kinase-2,3,6, dorsomorphin is preferable.

These compounds can be purchased from SIGMA, Tocris bioscience, Stemgent, Merck Biosciences and the like.

In addition, antisense oligonucleotide and siRNA of mRNA for AMP-activated protein kinase or ALK-2,3,6 and the like can also be used as inhibitor of AMP-activated protein kinase and/or ALK-2,3,6. In this step, moreover, when an increase of differentiation factors belonging to the BMP family or secretion of those differentiation factors, from the cells under culture into the medium, is confirmed, antibody that neutralizes the activity of those differentiation factors, or Noggin, Chordin, Cerberus, Gremlin and the like, which are known to bind to BMP to inhibit its action, can also be used as an inhibitor of AMP-activated protein kinase and/or ALK-2, 3,6.

When an increase or secretion of activin exemplified in the above-mentioned step (3) as an activator of activin receptor-like kinase-4,7 by the cells under culture in this step is confirmed in the medium, an antibody known to neutralize the activity of activin, or follistatin known to bind to activin to inhibit its action can also be used as an inhibitor of AMP activated protein kinase and/or ALK-2,3,6.

While the concentration of an inhibitor of AMP-activated protein kinase and/or activin receptor-like kinase-2,3,6 in the medium is appropriately determined according to the kind of the inhibitor to be used, the concentration of dorsomorphin when used is generally 0.1-20 µM, preferably 0.2-5 µM.

As the inhibitor of activin receptor-like kinase (ALK)-4,5,7 to be used in this step, SB-431542, SB-505124 (2-(5-benzo[1,3]dioxol-5-yl-2-tert-butyl-3H-imidazol-4-yl)-6-methylpyridine hydrochloride), SB-525334 (6-[2-tert-butyl-5-(6-methyl-pyridin-2-yl)-1H-imidazol-4-yl]-quinoxaline), A-83-01 (3-(6-methyl-2-pyridyl)-N-phenyl-4-(4-quinolinyl)-1H-pyrazole-1-thiocarboxamide), GW6604, LY-580276 (2-(6-methyl-2-pyridinyl)-3-(4-fluorophenyl)-5,6-dihydro-4H-pyrrolo[1,2-b]pyrazole) and SD-208 (2-(5-chloro-2-fluorophenyl)-N-(pyridin-4-yl)pyrido[2,3-d]pyrimidin-4-amine) and the like can be mentioned.

These can be purchased from SIGMA, Tocris bioscience, Wako Pure Chemical Industries, Ltd. and the like. In addition, antisense oligonucleotide and siRNA of mRNA for ALK-4,5,7 can also be used as an ALK-4,5,7 inhibitor.

As the inhibitor of ALK-4,5,7 to be used in this step, SB-431542 (4-[4-(1,3-benzodioxol-5-yl)-5-(2-pyridinyl)-1H-imidazol-2-yl]-benzamide or hydrate thereof) is preferable. While the concentration of an inhibitor of activin receptor-like kinase-4,5,7 in the medium is appropriately determined according to the kind of the inhibitor to be used, the concentration of SB-431542 when used is generally, 0.1-50 µM, preferably 1-20 µM.

Examples of the cell growth factor to be used in this step include vascular endothelial cell growth factor (VEGF), hepatocyte growth factor (HGF), stem cell growth factor (SCF), epithelial cell growth factor (EGF), various fibroblast growth factor (a/bFGF) and the like. Particularly preferred is basic fibroblast growth factor (bFGF).

While the concentration of the cell growth factor in the medium is appropriately determined according to the kind of the factor to be used, the concentration of bFGF when used is generally 1-200 ng/ml, preferably 20-100 ng/ml.

This step is performed in a medium containing all 4 kinds of components of the above-mentioned retinoic acid receptor agonist, an inhibitor of AMP activated protein kinase and/or activin receptor-like kinase-2,3,6, an inhibitor of activin receptor-like kinase-4,5,7 and a cell growth factor.

In this step, the retinoic acid receptor agonist, an inhibitor of AMP activated protein kinase and/or activin receptor-like kinase-2,3,6, an inhibitor of activin receptor-like kinase-4,5,7 and a cell growth factor may be simultaneously added to the medium or added to the medium with specific time difference as long as differentiation into progenitor cells of pancreatic hormone-producing cells can be induced. The retinoic acid receptor agonist, an inhibitor of AMP activated protein kinase and/or activin receptor-like kinase-2,3,6, an inhibitor of activin receptor-like kinase-4,5,7 and a cell growth factor are conveniently and preferably added simultaneously to the medium.

The medium to be used in this step is produced by adding a retinoic acid receptor agonist, an inhibitor of AMP activated protein kinase and/or activin receptor-like kinase-2,3,6, an inhibitor of activin receptor-like kinase-4,5,7 and a cell growth factor to a basal medium exemplified in the aforementioned step (2).

The medium to be used in this step may be prepared by using the same kind of a basal medium as the above-mentioned step (4), or using a different basal medium. Since induction of differentiation into progenitor cells of pancreatic hormone-producing cells can be performed more efficiently, Improved MEM Zinc Option medium (Invitrogen) is preferably used as the basal medium for this step.

In this step, it is preferable not to substantially use feeder cells and/or a feeder cell extract, and more preferable not to use feeder cells and/or a feeder cell extract at all.

When feeder cells and a feeder cell extract are not substantially used, a substance (e.g., animal-derived cells) causing rejection is contained in a less amount.

As the medium to be used in this step, a medium substantially free of serum and/or serum extract is preferable, and a serum-free medium is more preferable.

The medium to be used in this step may also contain a serum replacement.

Examples of the serum replacement include albumin, transferrin, fatty acid, collagen precursor, trace element (e.g., zinc, selenium), B-27 supplement, N2 supplement, knockout serum replacement, 2-mercaptoethanol, 3'-thiolglycerol, or equivalents thereof. The serum replacement to be used in this step is preferably B-27 supplement.

The concentration of the serum replacement in the medium, when B27 is used, is 0.01-10 wt %, preferably, 0.1-2 wt %.

This step is performed by cultivating at a culture temperature suitable for culture of an endodermal cell to be used, which is generally 30-40° C., preferably about 37° C., for 72-288 hr, preferably 120-216 hr, in a $CO_2$ incubator aerated with 1-10%, preferably 5%, of carbon dioxide.

In this step, differentiation induction of endodermal cells into progenitor cells of pancreatic hormone-producing cells can be confirmed by evaluating the presence or absence of the expression of protein and gene that show progenitor cells of pancreatic hormone-producing cells-specific expression (marker for progenitor cells of pancreatic hormone-producing cells). The expression of protein can be evaluated by the method utilizing an antigen-antibody reaction and the like, and the expression of gene can be evaluated by the method utilizing RT-PCR and the like. Examples of the marker include NGN3, HNF6 (hepatocyte nuclear factor 6, aka: one cut homeobox 1), PDX1 (pancreatic and duodenal homeobox 1) and the like.

Step (6): a Step of Cultivating the Cells Obtained in the Aforementioned Step (5)

This step corresponds to a step of inducing differentiation of progenitor cells of pancreatic hormone-producing cells into pancreatic hormone-producing cells.

The basal medium to be used in this step may be one exemplified in the aforementioned step (2). The basal medium to be used in this step may be prepared by using the same kind of a basal medium in the above-mentioned step (5), or using a different basal medium. Since induction of differentiation into pancreatic hormone-producing cells can be performed more efficiently, Improved MEM Zinc Option medium (Invitrogen) is preferably used as the basal medium for this step.

In this step, it is preferable not to substantially use feeder cells and/or a feeder cell extract, and more preferable not to use feeder cells and/or a feeder cell extract at all.

When feeder cells and a feeder cell extract are not substantially used, a substance (e.g., animal-derived cells) causing rejection is contained in a less amount.

As the medium to be used in this step, a medium substantially free of serum and/or serum extract is preferable, and a serum-free medium is more preferable.

The medium to be used in this step may also contain a serum replacement. Examples of the serum replacement include albumin (e.g., lipid rich albumin), transferrin, fatty acid, collagen precursor, trace element (e.g., zinc, selenium), B-27 supplement, N2 supplement, knockout serum replacement, 2-mercaptoethanol, 3'-thiolglycerol, or equivalents thereof. Of these, B-27 supplement is preferable. Particularly, Improved MEM Zinc Option medium (Invitrogen) added with B-27 supplement is preferably used. The concentration of the B-27 supplement in the medium is 0.01-10 wt %, preferably 0.1-2 wt %. In addition, an additive to improve cell's survival rate may be added to the Improved MEM Zinc Option medium. Examples of such additive include serum replacements such as knockout serum replacement, N2 supplement and the like, and the like. The concentration of the aforementioned additive in the medium is 0.01-10 wt %, preferably 0.1-2 wt %.

Preferably, the medium to be used in this step does not contain a retinoic acid receptor agonist, an inhibitor of AMP activated protein kinase and/or activin receptor-like kinase-2,3,6, an inhibitor of activin receptor-like kinase-4,5,7, and a cell growth factor. Therefore, it is preferable to exchange the media between step (5) and step (6).

This step is performed by cultivating at a culture temperature suitable for culture of progenitor cells of pancreatic hormone-producing cells to be used, which is generally 30-40° C., preferably about 37° C., for 24-240 hr, preferably 72-192 hr, in a $CO_2$ incubator aerated with 1-10%, preferably 5%, of carbon dioxide.

In this step, differentiation induction of progenitor cells of pancreatic hormone-producing cells into pancreatic hormone-producing cells can be confirmed by evaluating the expression of protein and gene (pancreatic hormone-producing cells marker) that show pancreatic hormone-producing cells-specific expression or measuring the amount of pancreatic hormone secreted in the medium. Examples of the marker include insulin, glucagon, pancreatic polypeptide, somatostatin, PCSK1 (proprotein convertase subtilisin/kexin type 1), SUR1 (sulfonylurea receptor 1, aka: ATP-binding cassette, sub-family C(CFTR/MRP), member 8), NKX6.1 (NK6 homeobox 1), PAX6 (paired box 6), NEUROD (neurogenic differentiation 1), ARX (aristaless related homeobox) and the like.

As mentioned above, the present invention provides a method of producing pancreatic hormone-producing cells from stem cells. By a similar method, i.e., a method of inducing differentiation of cells in a less differentiated state into a more differentiated state, differentiations of stem cells into cells in various differentiated states (endodermal cell, pancreatic duct cell, pancreatic endocrine cell, pancreatic exocrine cell, cell progenitor common thereto etc.) can be induced. The level of induced differentiation can be known by confirming the presence or absence of expression of a protein or gene that expresses specifically to each cell.

Using the production method of the present invention, differentiation of stem cells into pancreatic hormone-producing cells can be efficiently induced, whereby pancreatic hormone-producing cells having high pancreatic hormone secretion capability can be supplied in large amounts. The pancreatic hormone-producing cells can be utilized as a tool for developing a medicament (particularly a medicament for cell therapy) or a therapeutic drug for diabetes.

2. Medicament Comprising Cells of the Present Invention

The present invention provides a medicament comprising pancreatic hormone-producing cells (cells of the present invention) produced by the above-mentioned production method of the present invention or production method 2 of the present invention.

Furthermore, the present invention provides a medicament (sometimes to be abbreviated as a medicament of the present invention in the present specification) comprising progenitor cells of pancreatic hormone-producing cells produced by the above-mentioned production method of the present invention (preferably steps (1) to (5)) or production method 2 of the present invention.

In the medicament of the present invention, the pancreatic hormone-producing cells or progenitor cells of pancreatic hormone-producing cells are used as they are, or a cell mass such as concentrated pellets and the like, by filter filtration and the like, and the like. Furthermore, the medicament added with a protectant such as DMSO (dimethyl sulfoxide) and the like can also be cryopreserved. For safer utilization as the medicament, the medicament may be subjected to a treatment such as heat treatment, radiation treatment and the like, under the conditions that denature the pathogenic protein while maintaining its function as pancreatic hormone-producing cells or function as progenitor cells of pancreatic hormone-producing cells. To prevent growth of pancreatic hormone-producing cells or progenitor cells of pancreatic hormone-producing cells in an amount more than necessary, the cells may be subjected to a treatment in combination with the above-mentioned treatments, such as growth suppression by pre-treatment with mitomycin C and the like, a method including introducing a metabolic enzyme gene naturally absent in mammals into the cells, administering, where necessary, a non-active drug to allow the drug to change to a toxin only in the cells introduced with the metabolism enzyme gene naturally absent in mammals to cause death of the cells (suicide gene therapy) and the like.

The medicament of the present invention is safe and low toxic, and can be administered (transplanted) to a mammal (e.g., human, mouse, rat, guinea pig, swine, monkey etc., preferably human).

The dose (amount to be transplanted) of the medicament of the present invention is, for example, $1 \times 10^5$-$1 \times 10^{10}$ cells/individual, preferably, $5 \times 10^7$-$1 \times 10^{10}$ cells/individual, more preferably, $1 \times 10^9$-$1 \times 10^{10}$ cells/individual. For the medicament of the present invention, pancreatic hormone-producing cells prepared using patient's own cells or cells of donor showing cytocompatibility or histocompatibility type tolerable for the patient are preferably used. When sufficient cells cannot be achieved due to the age, constitution and the like, transplantation is also possible by embedding the cells in a capsule such as polyethylene glycol and silicon, a porous container and the like to avoid rejection. In this case, intraperitoneal or subcutaneous transplantation is also possible. The dose (amount to be transplanted) of the medicament of the present invention can be appropriately changed according to the age, body weight, symptom and the like of the patients who receive the administration.

Of the medicaments of the present invention, a medicament containing pancreatic hormone-producing cells enables production (secretion) of a pancreatic hormone in the body of patient by administration (transplantation) thereof, and is useful for the treatment of a disease caused by a decreased production (secretion) of the pancreatic hormone. For example, a medicament containing insulin-producing cells is useful for the treatment of diabetes (type I and type II, preferably type I or type II with decreased insulin level, particularly preferably type I). On the other hand, of the medicaments of the present invention, a medicament containing progenitor cells of pancreatic hormone-producing cells is, after administration (transplantation) to a patient, induced to differentiate into pancreatic hormone-producing cells under suitable conditions, wherein pancreatic hormone is produced (secreted).

3. Screening Method

The present invention provides a method of screening for a medicament (preferably therapeutic drug for diabetes), comprising using the cells obtained by any one or more steps selected from the group consisting of the following steps (1)-(6):

(1) a step of cultivating stem cells in a medium containing a Rho kinase inhibitor
(2) a step of cultivating the cells obtained in the aforementioned step (1) in a medium containing a GSK3 inhibitor
(3) a step of cultivating the cells obtained in the aforementioned step (2) in a medium containing GSK3 inhibitor and an activator of activin receptor-like kinase-4,7
(4) a step of forming a cell mass from the cells obtained in the aforementioned (3), and cultivating the cell mass in a suspension state in a medium
(5) a step of cultivating the cells obtained in the aforementioned step (4) in a medium containing a retinoic acid receptor agonist, an inhibitor of AMP-activated protein kinase and/or activin receptor-like kinase-2,3,6, an inhibitor of activin receptor-like kinase-4,5,7 and a cell growth factor
(6) a step of cultivating the cells obtained in the aforementioned step (5).

The above-mentioned steps (1)-(6) can be performed in the same manner as in the above-mentioned steps (1)-(6) of the production method of the pancreatic hormone-producing cells of the present invention.

As the cells to be used for the screening, the pancreatic hormone-producing cells obtained via the above-mentioned steps (1)-(6); the progenitor cells of pancreatic hormone-producing cells obtained via the above-mentioned steps (1)-(5); the endodermal cells obtained via the above-mentioned step (1)-(4) or the above-mentioned step (1)-(3); the cells obtained via the above-mentioned step (1)-(2); the cells obtained via the above-mentioned step (1) can be mentioned.

The screening method of the present invention is specifically performed as follows (embodiment 1). A method wherein (a) pancreatic hormone-producing cells are cultured in the presence of a test compound and (b) pancreatic hormone-producing cells are cultured in the absence of a test compound, an intracellular pancreatic hormone expression level and an extracellular pancreatic hormone secretion level are each measured, and compared.

As the expression level of pancreatic hormone, an expression level of a pancreatic hormone protein, an expression level of polynucleotide (e.g., mRNA and the like) encoding a pancreatic hormone protein and the like can be mentioned. The expression level and secretion level of a pancreatic hormone can be measured by a known method, for example, the aforementioned pancreatic hormone present in a cell extract, a medium and the like can be measured using an antibody recognizing a pancreatic hormone and according to a method such as Western blotting analysis, ELISA method and the like or a method analogous thereto and the like.

The mRNA level can be measured by a known method, for example, Northern hybridization, S1 mapping method, PCR method, DNA chip or array method or a method analogous thereto.

A pancreatic hormone-producing cell culture is not particularly limited as long as it is performed under conditions where a pancreatic hormone can be expressed and/or secreted and can be performed according to a known method. Examples of a usable medium include MEM medium containing about 1-20% fetal bovine serum [Science, vol. 122, 501 (1952) etc.], DMEM medium [Virology, vol. 8, 396 (1959)], RPMI 1640 medium [The Journal of the American Medical Association vol. 199, 519 (1967)], and 199 medium [Proceeding of the Society for the Biological Medicine, vol. 73, 1 (1950)]. The pH of the medium is preferably about 6-8. Culture is performed at generally about 30° C.-40° C. for about 15 hr-5 days with aeration and stirring as necessary.

Examples of the test compound include peptide, protein, antibody, nonpeptidic compound, synthetic compound, fermentation product, cell extract, plant extract, animal tissue extract, plasma. Here, the test compound may form a salt. As the salt, a salt with physiologically acceptable acid, base (e.g., alkali metal salt, alkaline earth metal salt, aluminum salt) and the like is used. Examples of such salt include salts with inorganic acid (e.g., hydrochloric acid, phosphoric acid, hydrobromic acid, sulfuric acid), salts with organic acid (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid), sodium salt, potassium salt, calcium salt, magnesium salt, barium salt and aluminum salt.

For example, a test compound that suppresses (inhibits) the expression level or secretion level of a pancreatic hormone in the above-mentioned (a) by not less than about 20%, preferably not less than about 30%, more preferably not less than about 50%, as compared to those of the above-mentioned (b), can be selected as a compound that suppresses (inhibits) expression of pancreatic hormone in pancreatic hormone-producing cells.

A test compound that enhances the expression level or secretion level of a pancreatic hormone in the above-mentioned (a) by not less than about 20%, preferably not less than about 30%, more preferably not less than about 50%, as compared to those in the above-mentioned (b), can be selected as a compound that enhances expression or secretion of pancreatic hormone in pancreatic hormone-producing cells.

When the pancreatic hormone-producing cells are insulin-producing cells, a compound that enhances insulin expression is useful as a therapeutic drug for diabetes. When the pancreatic hormone-producing cells are glucagon-producing cells, a compound that suppresses (inhibits) glucagon expression is useful as a therapeutic drug for diabetes.

Another embodiment of the screening method of the present invention is a method wherein (a) pancreatic hormone-producing cells are cultured in the presence of a test compound and (b) pancreatic hormone-producing cells are cultured in the absence of a test compound, a proliferative capacity of the cells is measured, and compared (embodiment 2). As the test compound to be used, those similar to the test compounds used in the above-mentioned embodiment 1 can be mentioned. The cell culture in this embodiment can be performed in the same manner as in the above-mentioned embodiment 1. As a method for measuring the proliferative capacity of cells, a method generally used in this field can be used and includes, for example, a method of counting cell number, a method of evaluating uptake of $^3$H, 5-bromo-2'-deoxy-uridine (BrdU) and the like, ATP level, conversion level of tetrazolium compound to formazan product and the like.

For example, when the pancreatic hormone-producing cells are insulin-producing cells, a compound that significantly enhances growth of insulin-producing cells is useful as a therapeutic drug for diabetes. When the pancreatic hormone-producing cells are glucagon-producing cells, a compound that significantly suppresses (inhibits) growth of glucagon-producing cells is useful as a therapeutic drug for diabetes.

Another embodiment of the screening method of the present invention is a method wherein (a) progenitor cells of pancreatic hormone-producing cells are cultured in the presence of a test compound and (b) progenitor cells of pancreatic hormone-producing cells are cultured in the absence of a test compound, the level of differentiation of the cells is measured, and compared (embodiment 3). As the test compound to be used, those similar to the test compounds used in the above-mentioned embodiment 1 can be mentioned. The cell culture in this embodiment can be performed in the same manner as in the above-mentioned embodiment 1. The level of differentiation of progenitor cells of pancreatic hormone-producing cells can be examined by, for example, the presence or absence of expression of a marker specific to progenitor cells of pancreatic hormone-producing cells and/or pancreatic hormone-producing cells. Examples of the marker specific to progenitor cells of pancreatic hormone-producing cells include NGN3 (neurogenin 3), PAX4 (paired box 4), and examples of the marker specific to pancreatic hormone-producing cells include insulin, glucagon, pancreatic polypeptide, somatostatin, ghrelin, PCSK1 (proprotein convertase subtilisin/kexin type 1), SUR1 (sulfonylurea receptor 1, aka ATP-binding cassette, sub-family C(CFTR/MRP), member 8), glucokinase, MAFA (v-maf musculoaponeurotic fibrosarcoma oncogene homolog A), IAPP (islet amyloid polypeptide) and the like.

For example, when the progenitor cells of pancreatic hormone-producing cells are progenitor cells of insulin-producing cells, a compound that significantly enhances differentiation of progenitor cells of insulin-producing cells is useful as a therapeutic drug for diabetes. When the progenitor cells of pancreatic hormone-producing cells are progenitor cells of glucagon-producing cells, a compound that significantly suppresses (inhibits) differentiation of progenitor cells of glucagon-producing cells is useful as a therapeutic drug for diabetes.

Another embodiment of the screening method of the present invention is a method wherein (a) endodermal cells are cultured in the presence of a test compound and (b) endodermal cells are cultured in the absence of a test compound, a proliferative or differentiation capacity of the cells is measured, and compared (embodiment 4). As the test compound to be used, those similar to the test compounds used in the above-mentioned embodiment 1 can be mentioned. The cell culture in this embodiment can be performed in the same manner as in the above-mentioned embodiment 1. As a method for measuring the proliferative capacity of cells, a method generally used in this field can be used and includes, for example, a method of counting cell number, a method of evaluating uptake of $^3$H, 5-bromo-2'-deoxy-uridine (BrdU) and the like, ATP level, conversion level of tetrazolium compound to formazan product and the like. The differentiation capacity of endodermal cells can be examined by, for example, the presence or absence of expression of a marker specific to endodermal cells. Examples of the marker specific to endodermal cells include α-fetoprotein, albumin, pepsin, pulmonary surfactant protein and the like. In general, differentiation induction and culture of endodermal cells are technically difficult as compared to those of mesodermal or ectodermal cells, and cells and/or endoderm differentiation-induction system prepared by utilizing a compound obtained by the screening method can be used for a new screening system for medicaments.

A medicament etc. that protect (maintain) function of pancreatic hormone-producing cells can be obtained by a method according to the screening method of the present invention. Another embodiment of the screening method of the present invention is a method wherein (a) pancreatic hormone-producing cells are cultured in the presence of a test compound and (b) pancreatic hormone-producing cells are cultured in the absence of a test compound, the number or function of viable cells are respectively measured, and compared (embodiment 5). As the test compound to be used, those similar to the test compounds used in the above-mentioned embodiment 1 can be mentioned. The cell culture in this embodiment can be performed in the same manner as in the above-mentioned embodiment 1. As a method for counting the viable cells, a method generally used in this field can be used and includes, for example, a method of counting cell number, a method of evaluating uptake of $^3$H, 5-bromo-2'-deoxy-uridine (BrdU) and the like, ATP level, conversion level of tetrazolium compound to formazan product and the like. In addition, the number of cells after induction of apoptosis can be quantified by, in addition to counting of the cells showing morphological characteristics (chromatin aggregation, nucleus fragmentation, cell contraction and the like), detection of fragmented DNA by TUNNEL (TdT-mediated dUTP nick end labeling) method and detection of the presence or absence of active caspase, and measurement of nuclear staining with live-cell impermeant dye such as 7-AAD (7-amino-actinomycin D) and the like, exposure of phosphatidylserine on cell surface, depolarization of mitochondria membrane, cleavage and degradation of particular intracellular protein and the like. As a method of determining the cell function, a method of measuring secretion level of insulin or C-peptide and variation in cellular membrane potential, which correspond to the glucose concentration, and the like can be mentioned. In this embodiment, a factor known to cause disorder in pancreatic hormone-producing cells, for example, inflammatory cytokine, active oxygen and production inducing substance thereof, high concentration of fatty acid, glucose and the like, is added during cell culture, and the number of viable cells or function of the cells is measured, and compared.

When pancreatic hormone-producing cells are insulin-producing cells, a compound that significantly enhances survival or functional maintenance of the insulin-producing cells against a factor known to cause disorder of the pancreatic hormone-producing cells is useful as a therapeutic drug for diabetes.

The medicament obtained by the screening method of the present invention can be formulated by a conventional means and using a physiologically acceptable additive (e.g., carrier, flavor, excipient, preservative, stabilizer, binder).

Examples of the dosage form of the thus-obtained preparation include oral preparations such as tablet applied with sugar coating as necessary, capsule, elixir, microcapsule and the like; and parenteral agents such as injection and the like. The content of the active ingredient in these preparations is, for example, 0.1-90 wt %.

Examples of the aforementioned additives include binders such as gelatin, cornstarch, tragacanth, gum arabic and the like; excipients such as crystalline cellulose and the like; swelling agents such as cornstarch, gelatin, alginic acid and the like; lubricants such as magnesium stearate and the like; sweetening agents such as sucrose, lactose, saccharin and the like; flavors such as peppermint, Gaultheria adenothrix oil, cherry and the like; liquid carriers such as fats and oils, water for injection, vegetable oil (e.g., sesame oil, palm oil, soybean oil), buffering agent (e.g., phosphate buffer, sodium acetate buffer) and the like; solubilizing agents (e.g., ethanol, propylene glycol, polyethylene glycol); non-ionic surfactant (e.g., polysorbate 80™, HCO-50); solubilizing agents (e.g., benzyl benzoate, benzyl alcohol); soothing agents (e.g., benzalkonium chloride, procaine hydrochloride); stabilizers (e.g., human serum albumin, polyethylene glycol); preservatives (e.g., benzyl alcohol, phenol); and antioxidants.

Examples of the aforementioned water for injection include saline; and an isotonic solution containing glucose, D-sorbitol, D-mannitol, sodium chloride or the like.

Since a medicament (preferably therapeutic drug for diabetes) obtained by the screening method of the present invention is safe and low toxic, it can be administered orally or parenterally to, for example, a mammal (e.g., human, mouse, rat, rabbit, sheep, swine, bovine, horse, cat, dog, monkey, chimpanzee).

The dose of the medicament is appropriately determined according to its action, the target disease, subject of administration, administration route and the like.

EXAMPLES

The present invention is explained in detail in the following by referring to Examples, which are not to be construed as limitative.

Example 1 (1)

Induction of Differentiation of Human iPS Cells into Endodermal Cells

Steps (1)-(3)

Induction of differentiation of human iPS cells into endodermal cells was performed by the following method.

First, human iPS cells (iPS cells obtained by introducing Oct3/4gene, Klf4 gene and Sox2 gene: see Nat Biotechnol 2008; 26: 101-106) cultured and maintained in the state of a cell mass together with feeder cells were detached in the state of a cell mass by using a cell dissociation solution for primate ES cell (ReproCELL Inc.), these cells were transferred into a 15 ml centrifuge tube and stood for 5 min. The feeder cells were removed by removing the supernatant.

To the human iPS cells sedimented in the centrifuge tube, 0.25% trypsin-1 mM EDTA solution (GIBCO) was added, and allowed to dissociate until they form singulated cells. Then, human iPS cells dispersed in a medium were seeded at a density of $15 \times 10^4$ cells per one 100 mm dish coated with BD Matrigel (Nippon Becton Dickinson Company, Ltd.), and cultured at 37° C., 5% $CO_2$ for 1 day. The 100 mm dish used was one coated with BD Matrigel diluted 40-fold with serum-free DMEM/F12 medium (Invitrogen), at room temperature for 3 hr or longer. As a medium for dispersion and seeding was a medium for primate ES cell (ReproCELL Inc.) added with 10 µM Y-27632 (Wako Pure Chemical Industries, Ltd.). One day after seeding, the medium was exchanged with DMEM/F12 medium containing a GSK3β inhibitor CHIR99021 (3 µM) and 2% B-27 supplement (GIBCO) and cultured for 2 days. Then the medium was exchanged with DMEM/F12 medium containing activin A (50 ng/ml) and CHIR99021 (1 µM) and cultured for 2 days.

To examine variation in the expression of endoderm differentiation markers when human iPS cells were cultured, the cells after differentiation induction were recovered over time, and total RNA fraction was purified using RNeasy96 (Qiagen). cDNA was synthesized using PrimeScriptRT reagent kit (Takara Bio Inc.), quantitative RT-PCR was performed, and the gene expression level of a primitive streak marker Brachyury, and an endoderm marker SOX17 was measured. The results of expression analysis are shown in FIG. 1. On day 3 of culture, the expression level of Brachyury increased temporarily, and the expression level of SOX17 remarkably increased on day 4. Therefrom it has been clarified that the expression of endoderm marker was efficiently induced via differentiation into primitive streak.

Figure 2:
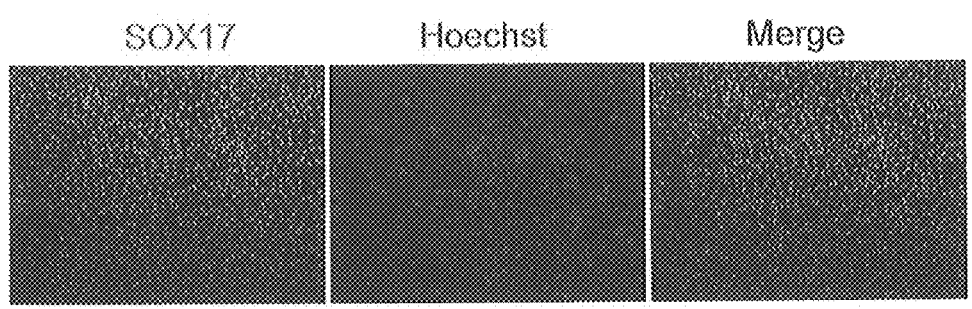
FIG. 2 shows the results of immunofluorescent staining, using an anti-human SOX17 antibody, of the cells obtained by inducing differentiation of human iPS cells for 4 days using activin A and CHIR99021, re-plating the cells on a 96-well plate coated with fibronectin, and culturing the cells for 1 day. The nuclei of SOX17-positive cells were colored green with Alexa 488 (SOX17 in the Figure), and the nuclei of cells were colored blue with Hoechst 33342 (Hoechst in the Figure). In addition, both stained images were combined and shown as Merge. Most cells were observed to express SOX17 protein.

To examine the expression of SOX17 protein, immunofluorescent staining was performed using an anti-SOX17 antibody. Endodermal cells obtained by differentiation induction in a 100 mm dish were dissociated into singulated cells using Accutase (Invitrogen) (trade name), seeded in a fibronectin-coated 96-well plate at a density of $4 \times 10^4$ cells, and cultured at 37° C., 5% $CO_2$ for 1 day. The fibronectin coating was performed by diluting fibronectin (BD) 20-fold with DMEM/F12, and standing same at room temperature for 3 hr. As a culture medium for seeding, Improved MEM Zinc Option medium (Invitrogen) containing 1% B-27 supplement was used. After culture, 4% para-formaldehyde was added and the cells were fixed by incubating at room temperature for 30 min. The cells after culture were successively reacted with anti-human SOX17 antibody (AF1924, R&D) as a primary antibody and then with Alexa488-labeled secondary antibody (Invitrogen) as a secondary antibody, the cell nucleus was stained with Hoechst 33342, and observed with a fluorescence microscope. The results are shown in FIG. 2. As a result, most of the cells expressed SOX17 protein. From the foregoing study, it has been clarified that differentiation into endodermal cells can be efficiently induced by cultivating for 2 days in DMEM/F12 medium added with CHIR99021 and B-27 supplement, and further for 2 days in DMEM/F12 medium added with activin A and CHIR99021, without using feeder cells and serum.

Example 1 (2)

Endoderm Induction by GSK3 Inhibitor (BIO) Other than CHIR99021 in Step (2) was Studied One day after seeding of human iPS cells, the medium was exchanged with DMEM/F12 medium containing CHIR99021 (3 µM) and 2% B-27 supplement (GIBCO), and cultured for 2 days.

Figure 3:
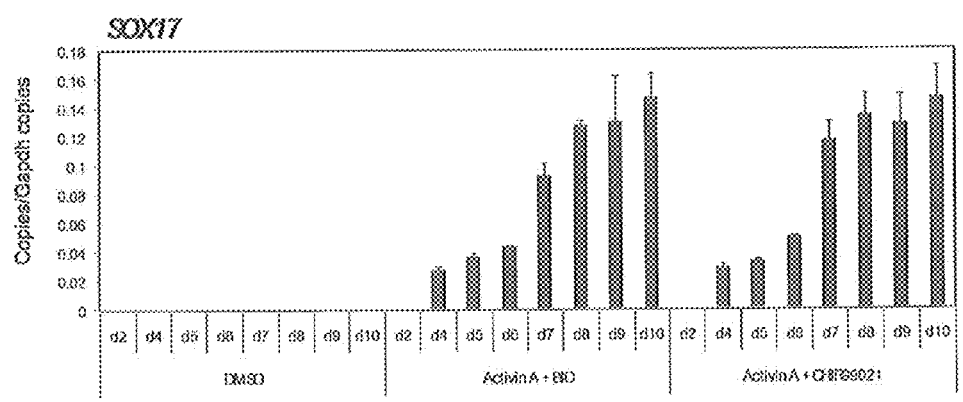
FIG. 3 shows the results of SOX17 expression by human iPS cells, which had been cultured in a medium containing CHIR99021 for 2 days, and then cultured using activin A and CHIR99021, as well as activin A and BIO, as measured by quantitative RT-PCR every day. The expression levels of gene are shown as relative values to the expression level of a housekeeping gene GAPDH. Whether using CHIR99021 or BIO, the SOX17 expression increased over time from day 4 of culture, and showed a similar expression pattern. In the control added with only DMSO, the SOX17 expression did not increase.

Then, one was exchanged with DMEM/F12 medium containing CHIR99021 (3 µM) as GSK3 inhibitor and activin A (100 ng/ml) and 2% B-27 supplement (GIBCO), and culture was continued (indicated as "Activin A+CHIR99021" in FIG. 3).

The other was exchanged with DMEM/F12 medium containing BIO (0.5 µM) as GSK3 inhibitor and activin A (100 ng/ml), and 2% B-27 supplement (GIBCO), and culture was continued (indicated as "Activin A+BIO" in FIG. 3).

The level of the gene expression of SOX17 when human iPS cells were cultured was measured over time. The results of expression analysis are shown in FIG. 3. Whether using CHIR99021 or BIO, the expression level of SOX17 remarkably increased from day 4 of culture, and a similar expression pattern was observed. The results have clarified that endoderm can be induced even by using a GSK3 inhibitor other than CHIR99021.

Example 2

Induction of Differentiation of Endodermal Cells into Pancreatic Hormone-Producing Cells Steps (4)-(6)

A cell mass was formed from cells differentiated into endodermal cells, after which further induced to differentiate into progenitor cells of pancreatic hormone-producing cells, then into pancreatic hormone-producing cells.

Using endodermal cells induced to differentiate in a 100 mm dish were dissociated until they form singulated cells by using Accutase (Invitrogen) (trade name). Then, endodermal cells dispersed in a medium were seeded at a density of $2\times10^4$ cells per well in a 96-well spheroid plate (SUMITOMO BAKELITE), and cultured at 37° C., 5% $CO_2$ for 1 day to form a cell mass. As a medium for dispersion and seeding, Improved MEM Zinc Option medium containing 1% B-27 supplement was used. One day from endodermal cell seeding, the medium was exchanged with Improved MEM Zinc Option medium containing 1% B-27 supplement and added with dorsomorphin (1 μM), retinoic acid (2 μM), SB431542 (10 μM) and bFGF (50 ng/ml), and cultured under the conditions of 37° C., 5% $CO_2$ for 8 days. Medium exchange was performed on day 4. After culture for 8 days, the medium was exchanged with Improved MEM Zinc Option medium containing 1% B-27 supplement and the cells were further cultured. Thereafter, the medium exchange was performed every 3 days-4 days.

Figure 4:
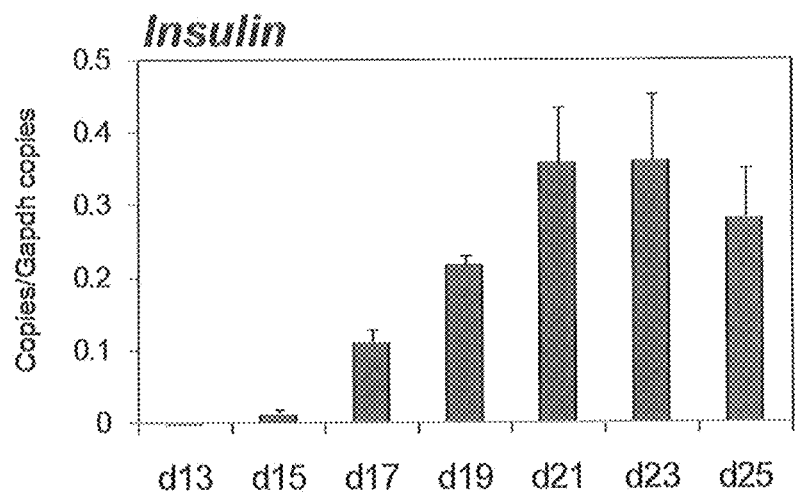
FIG. 4 shows the results of the analysis of insulin expression by the cells obtained by inducing differentiation of human iPS cells using activin A and CHIR99021 for 4 days, plating the cells on a 96-well spheroid plate, culturing the cells for 1 day, culturing the cells for 8 days in an Improved MEM Zinc Option medium containing 1% B27 and added with dorsomorphin, retinoic acid, SB431542 and bFGF, thereafter changing the medium to an Improved MEM Zinc Option medium containing 1% B27, and further continuously culturing the cells (Insulin in the Figure). The expression levels of gene are shown as relative values to the expression level of a housekeeping gene GAPDH. The expression of insulin increased from day 13 of culture in the Improved MEM Zinc Option medium containing 1% B27 and increased over time until day 23 of culture.

One day from endoderm seeding, cells were cultured with a combination of dorsomorphin, retinoic acid, SB431542 and bFGF for 8 days, the medium was exchanged with Improved MEM Zinc Option medium containing 1% B-27 supplement and the culture was continued. The results of analysis of the expression of insulin at that time are shown in FIG. 4. The expression of insulin was scarcely observed at the time point of day 13 of culture after the exchange of the medium with Improved MEM Zinc Option medium containing 1% B-27 supplement, but drastically increased from day 15 of culture.

Figure 5:
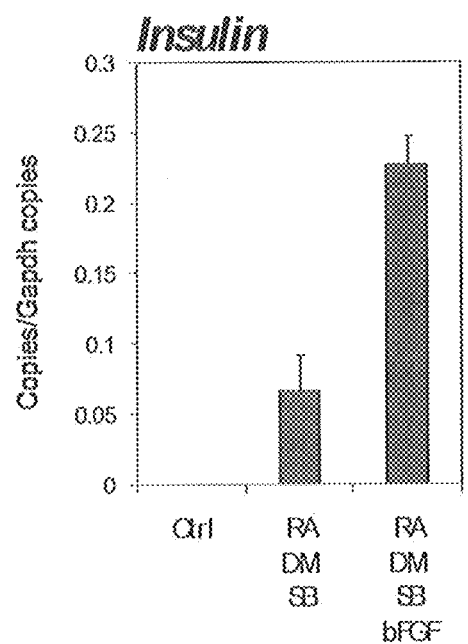
FIG. 5 shows the results of the analysis of insulin expression by the cells on day 19 of culture, which cells were obtained by inducing differentiation of human iPS cells using activin A and CHIR99021 for 4 days, plating the cells on a 96-well spheroid plate, culturing the cells for 1 day, culturing the cells for 8 days using a combination of dorsomorphin, retinoic acid, SB431542 and bFGF, or a combination of dorsomorphin, retinoic acid and SB431542, and thereafter culturing in an Improved MEM Zinc Option medium containing 1% B27 (Insulin in the Figure). The expression levels of gene are shown as relative values to the expression level of a housekeeping gene GAPDH. The expression level of insulin was higher on day 19 of culture by using a combination of dorsomorphin, retinoic acid, SB431542 and bFGF than a combination of dorsomorphin, retinoic acid and SB431542.

As comparative example, endodermal cells were seeded, one day later, the cells were cultured using a combination of dorsomorphin, retinoic acid and SB431542 for 8 days, the medium was exchanged with Improved MEM Zinc Option medium containing 1% B-27 supplement and the cells were further cultured. The results of expression analysis on day 19 of culture are shown in FIG. 5. The insulin expression showed a high value on day 19 of culture when cultivated using a combination of dorsomorphin, retinoic acid, SB431542 and bFGF, than culture using a combination of dorsomorphin, retinoic acid and SB431542.

Figure 6:
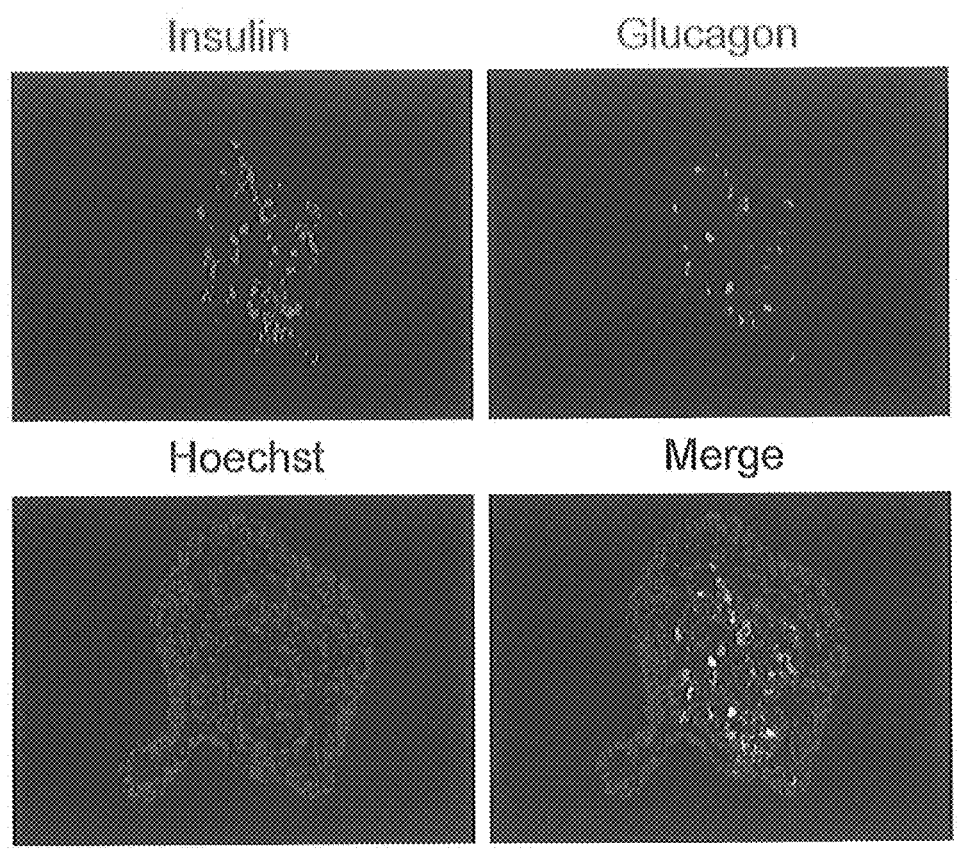
FIG. 6 shows the results of immunofluorescent staining, using anti-insulin antibody and anti-glucagon antibody, of a frozen section prepared from a cell mass (sphere) on day 21 of culture of the cells obtained by inducing differentiation in the same manner as in the method of FIG. 4. The insulin-positive cells were colored red with Alexa568 (Insulin in the Figure), the glucagon-positive cells were colored green with Alexa 488 (Glucagon in the Figure), and the nuclei of cells were colored blue with Hoechst 33342 (Hoechst in the Figure). In addition, all stained images were combined and shown as Merge. Many cells expressing insulin were found within the cell mass (sphere), and a part of the cells expressed glucagon.

Then, to examine protein expression of insulin and glucagon, immunofluorescent staining using an anti-insulin antibody was performed. One day after endodermal cell seeding, dorsomorphin, retinoic acid, SB431542 and bFGF were added and the cells were cultured for 8 days. Then, the medium was exchanged with Improved MEM Zinc Option medium containing 1% B-27 supplement and cultured for 8 days. After culture, the cells were fixed at 4° C. for 3 hr using 4% para-formaldehyde, the cultured cells were embedded in OCT compound (Tissue-tek) to prepare a 10 μm-thick frozen section. The cells were successively reacted with anti-insulin antibody (A0564, DAKO) or anti-glucagon antibody (G2654, SIGMA) as a primary antibody, then with Alexa568-labeled secondary antibody (Invitrogen) or Alexa488-labeled secondary antibody (Invitrogen) as a secondary antibody, and the cell nucleus was stained with Hoechst 33342 and observed by a fluorescence microscope. The results of immunofluorescent staining are shown in FIG. 6. A number of cells expressing insulin were found inside of the sphere, and also, the cells expressing glucagon were partly found.

Example 3

Induction of Differentiation of Human iPS Cell into Pancreatic Hormone-Producing Cell Steps (1)-(6); Induction of Differentiation into Endodermal Cells Using BD Matrigel or Fibronectin, and Induction of Differentiation into Pancreatic Hormone-Producing Cells Induction of differentiation of human iPS cells into endodermal cells was performed by the following method.

First, human iPS cells maintained in the state of a cell mass were dissociated until they formed singulated cells in the same manner as in Example 1.

Then, human iPS cells dispersed in a medium were seeded at a density of $60\times10^4$ cells per one 100 mm dish coated with fibronectin (Invitrogen), and cultured at 37° C., 5% $CO_2$ for 1 day. The 100 mm dish used was one coated with fibronectin diluted 40-fold with serum-free DMEM/F12 medium (Invitrogen), at room temperature for 3 hr or longer. (indicated as "fibronectin" in FIG. 7)

Human iPS cells dispersed in a medium were seeded at a density of $15\times10^4$ cells per one 100 mm dish coated with BD Matrigel (Nippon Becton Dickinson Company, Ltd.), and cultured at 37° C., 5% $CO_2$ for 1 day. The 100 mm dish used was one coated with BD Matrigel diluted 40-fold with serum-free DMEM/F12 medium (Invitrogen), at room temperature for 3 hr or longer. (indicated as "Matrigel" in FIG. 7)

As a medium for dispersion and seeding was a medium for primate ES cell (ReproCELL Inc.) added with 10 μM Y-27632 (Wako Pure Chemical Industries, Ltd.). One day after seeding, the medium was exchanged with DMEM/F12 medium containing a GSK3β inhibitor CHIR99021 (3 μM) and 2% B-27 supplement (GIBCO) and cultured for 2 days. Then the medium was exchanged with DMEM/F12 medium containing activin A (50 ng/ml) and CHIR99021 (1 μM) and cultured for 2 days.

A cell mass was formed in the same manner as in Example 2 from the cells differentiated into endodermal cells, after which further induced to differentiate into progenitor cells of pancreatic hormone-producing cells, then into pancreatic hormone-producing cells.

Figure 7:
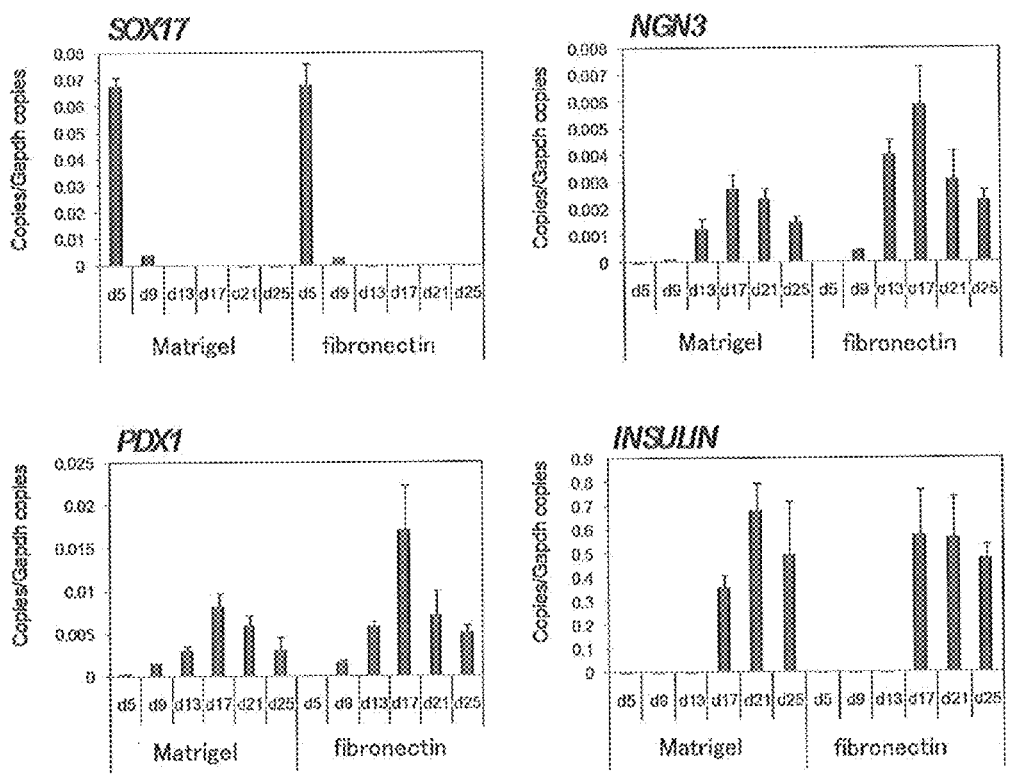
FIG. 7 shows the results of the analysis of expression of various differentiation markers in the cells obtained by inducing human iPS cells using BD Matrigel or fibronectin as a substrate, and activin A and CHIR99021 into endoderm to form a cell mass (sphere), and thereafter further inducing differentiation into progenitor cells of pancreatic hormone-producing cells and then pancreatic hormone-producing cells. The expression levels of respective genes were shown as relative values to the expression level of a housekeeping gene GAPDH. The expression of SOX17 remarkably decreased with differentiation, and the expressions of PDX1 and NGN3 gradually increased until day 17 of culture. The expression of insulin drastically increased from day 17 of culture. The variation of expression of these various differentiation markers over time was almost the same as long as the endodermal cells induced using BD Matrigel or fibronectin as a substrate were used.

In the same manner as in Example 2, one day from endodermal cell seeding, cells were cultures with a combination of dorsomorphin, retinoic acid, SB431542 and bFGF for 8 days, the medium was exchanged with Improved MEM Zinc Option medium containing 1% B-27 to induce differentiation, and analysis of time-course expression of various differentiation markers was performed. The results of expression analysis are shown in FIG. 7.

The expression of SOX17, which is an endoderm marker, remarkably decreased along with differentiation, and the expression of pancreatic progenitor cell marker (PDX1) and progenitor cells of pancreatic hormone-producing cell marker (NGN3) gradually increased up to day 17 of culture. The expression of insulin drastically increased from day 17 of culture. Such time-course variation in the expression of various differentiation markers was almost the same between endodermal cells induced using BD Matrigel as a substrate and endodermal cells induced using fibronectin as a substrate. BD Matrigel is a basal lamina product extracted from Engelbreth-Holm-Swarm (EHS) mouse sarcoma cells. On the other hand, fibronectin used in this Example was extracted from human plasma by affinity chromatography. Therefrom it has been clarified that differentiation into pancreatic hormone-producing cells can be induced even when fibronectin is used, as in the case of BD Matrigel (Examples 1 and 2).

Figure 8:
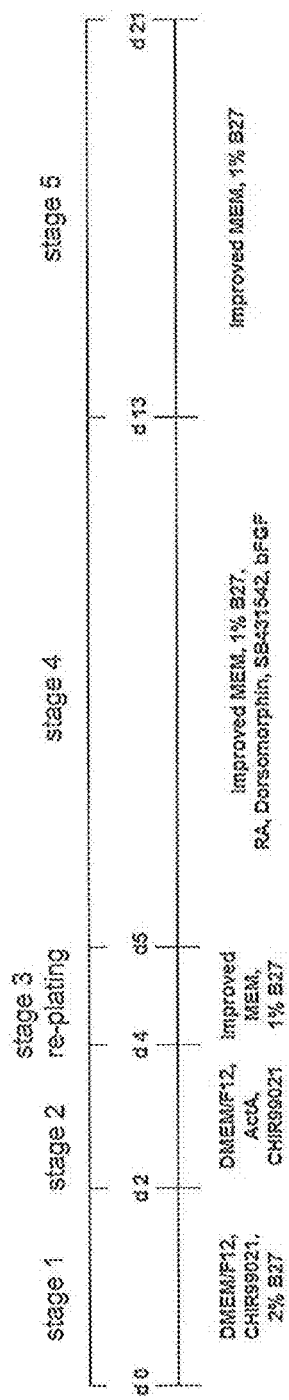
FIG. 8 shows an outline of a production method of a pancreatic hormone-producing cell, which includes a step of inducing differentiation by forming a cell mass (sphere) from endoderm [step (4)] and does not use a feeder cell or serum.

By studying Examples 1-3 above, it has been clarified that differentiation into pancreatic hormone-producing cells can be induced by using the pancreas differentiation induction system shown in FIG. 8 wherein a sphere is formed from endodermal cells, the cells are cultured for 8 days in Improved MEM Zinc Option medium containing 1% B-27 supplement added with dorsomorphin, retinoic acid, SB431542 and bFGF, then the medium is exchanged with Improved MEM Zinc Option medium containing 1% B-27 supplement and the cells are cultured.

The pancreatic hormone-producing cells produced by the method of the present invention are superior in the insulin production level to pancreatic hormone-producing cells produced by other methods.

INDUSTRIAL APPLICABILITY

According to the production method of the present invention, pancreatic hormone-producing cells in a form more mimicking the pancreatogenesis can be produced from a stem cell. In addition, the cell of the present invention can be used for screening for a compound useful for the prophylaxis and/or treatment of diseases caused by abnormal pancreatic hormone production and/or secretion such as diabetes and the like. Furthermore, since the cell of the present invention can be used for cell therapy for the treatment of such diseases and maintains a three-dimensional structure, it is more suitable for the application to cell therapy even when compared to pancreatic hormone-producing cells obtained according to a conventional production method.

This application is based on patent application No. 2010-178523 filed in Japan, the contents of which are incorporated in full herein.

The invention claimed is:

1. A method of producing human pancreatic hormone-producing cells, comprising subjecting human pluripotent stem cells to the following steps (1)-(6):

(1) a step of cultivating human pluripotent stem cells in a medium containing (+)-(R)-trans-4-(1-aminoethyl)-N-(4-pyridyl)cyclohexanamide dihydrochloride, (2) a step of cultivating the cells obtained in the aforementioned step (1) in a medium containing a 6-[[2-[[4-(2,4-dichlorophenyl)-5-(4-methyl-1H-imidazol-2-yl)-2-pyrimidinyl]amino]ethyl]amino]nicotinonitrile or (2'Z,3'E)-6-bromoindirubin-3'-oxime, (3) a step of cultivating the cells obtained in the aforementioned step (2) in a medium containing 6-[[2-[[4-(2,4-dichlorophenyl)-5-(4-methyl-1H-imidazol-2-yl)-2-pyrimidinyl]amino]ethyl]amino]nicotinonitrile and activin (4) a step of forming a cell mass from the cells obtained in the aforementioned (3), and cultivating the cell mass in a suspension state in a medium (5) a step of cultivating the cells obtained in the aforementioned step (4) in a medium containing dorsomorphin, retinoic acid, 4-[4-(1,3-benzodioxol-5-yl)-5-(2-pyridinyl)-1H-imidazol-2-yl]-benzamide or hydrate thereof and basic fibroblast growth factor, (6) a step of cultivating the cells obtained in the aforementioned step (5) to produce human pancreatic hormone-producing cells.

2. The production method according to claim 1, wherein the steps (1)-(6) do not substantially use a feeder cell.

3. The production method according to claim 1, wherein the medium in steps (1)-(6) does not substantially contain a serum.

4. The production method according to claim 1, wherein the pancreatic hormone-producing cells are any selected from the group consisting of insulin-producing cells, glucagon-producing cells, somatostatin-producing cells, pancreatic polypeptide (PP)-producing cells and ghrelin-producing cells.

* * * * *